United States Patent [19]

Titball et al.

[11] Patent Number: 5,985,285
[45] Date of Patent: Nov. 16, 1999

[54] VACCINES FOR PLAGUE

[75] Inventors: Richard W Titball; Ethel D Williamson; Sophie E C Leary; Petra C F Oyston; Alice M Bennett, all of Salisbury, United Kingdom

[73] Assignee: The Secretary of State for Defence in Her Britanic Majesty's Government of the United Kingdom of Great Britain and Northern Ireland, United Kingdom

[21] Appl. No.: 08/913,477

[22] PCT Filed: Mar. 13, 1996

[86] PCT No.: PCT/GB96/00571

§ 371 Date: Sep. 15, 1997

§ 102(e) Date: Sep. 15, 1997

[87] PCT Pub. No.: WO96/28551

PCT Pub. Date: Sep. 19, 1996

[30] Foreign Application Priority Data

Mar. 13, 1995 [GB] United Kingdom .................. 9505059
Sep. 15, 1995 [GB] United Kingdom .................. 9518946
Dec. 5, 1995 [GB] United Kingdom .................. 9524825

[51] Int. Cl.$^6$ ..................... A61K 39/02; A61K 39/102; A01N 63/00; C12P 21/06
[52] U.S. Cl. .............. 424/234.1; 424/93.4; 424/255.1; 424/184.4; 435/69.1; 435/69.3; 435/71.1; 435/172.3
[58] Field of Search ................................ 424/234.1, 93.2, 424/93.4, 192.1, 184.4, 255.1; 514/2; 435/69.1, 69.3, 822, 71.1, 172.3; 536/23.7

[56] References Cited

PUBLICATIONS

FEMS Immunology and Medical Microbiology, 12 (3–4), 1995 223–230., XP000573083 Williamson E D et al: "A new improved sub–unit vaccine for plague: The basis of protection" see the whole document.

Leary S E C et al: "Expression of *Yersinia pestis* V antigen in attenuated *Salmonella typhimurim*: Development of a novel vaccine for plague", Karger AG, 13 (0). 1995. 216–217., Basel, Switzerland XP000572863 in Ravagnan G & Chiesa C (eds): Yersiniosis: Present and Future.

Infection and Immunity, vol. 63, No. 2, Feb. 1995, Washington US, pp. 563–568, XP002006749 Oyston P C F et al.: "Immunization with live recombinant *Salmonella typhimurium* aroA producing F1 antigen protects against palgue" cited in the application see the whole document.

Infection and Immunity, vol. 62, No. 10, Oct. 1994, Washington US, pp. 4192–4201, XP002006750 Motin V L et al.: "Passive immunity to Yersiniae mediated by anti–recombinant V antigen and protein A–V antigen fusion peptide" see the whole document.

Simpson et al. Am. J. Trop. Med. Hyg. 43 (4): 389–396, 1990.

Burrows. Nature 179: 1246–1247, 1957.

Burrows et al. Br. J. Exp. Pathol. 39: 278–91, 1958.

Gremyakina et a. Mol. Gen. Mikrobiol. Virusol. VI, Jan.–Feb. 23–26, 1994.

Motin et al. In: Abstracts of the 94th General Meeting of the American Society for Microbiology, abstract E–68, pp. 155, 1994.

Price et al. J. Bacteriol. 173 (8): 2649–2657, 1991.

Brubaker, Contrib. Microbiol. Immunol. Basel, Karger, vol. 12, pp. 127–133, 1991.

Sato et al. Contrib. Microbiol. Immunol. Basel, Karger, vol. 12, pp. 225–229, 1991.

Meyer et al. J. Infect. Dis. 129 Suppl: S41–S45, 1974.

Lawton et al. J. Immunol. 91: 179–184, 1963.

Galyov et al. FEBS Lett. 277 (1, 2): 230–232, 1990.

Galyov et al. FEBS Lett. 286 (1, 2): 79–8, 1991.

Price et al. J. Bacteriol. 171 (10): 5646–5643, 1989.

Anisomov et al. Mol. Gen. Mikrobiol. Virusol. 2: 24–27, abstract, 1987.

Leary et al. Infect. Immun. 63: 2854–2858, 1995.

Une et al. J. Immunol. 133 (4): 226–230, 1984.

*Primary Examiner*—James C. Housel
*Assistant Examiner*—S. Devi
*Attorney, Agent, or Firm*—Nixon & Vanderhye

[57] ABSTRACT

A method of protecting a human or animal body from the effects of infection with *Y. pestis* is provided comprising administering to the body a vaccine including *Yersinia pestis* V antigen and *Yersinia pestis* F1 antigens or a protective epitopic part of each of these in a form other than whole *Y. Pestis* organisms. Preferably the antigens are administered in the form of a live vaccine or as recombinantly produced isolated and/or purified proteins. DNA encoding the whole or part of the F1 antigen and DNA encoding the whole or part of the V antigen may be used directly as a agnetic vaccine.

48 Claims, 2 Drawing Sheets

VACCINES FOR PLAGUE

This application is a 35 U.S.C. §371 of PCT/GB96/00571, filed Mar. 13, 1996.

The present invention relates to novel vaccines for provision of protection against infection with the organism *Yersinia pestis* and to methods for administering these. Particularly provided are parenterally and orally active vaccines capable of offering protection against bubonic and pneumonic plague. particularly by induction of mucosal immunity in both humans and other animals.

*Yersinia pestis* is the highly virulent causative organism of plague in a wide range of animals, including man. Infection with such organisms results in a high rate of mortality. Studies have shown that the high virulence is due to a complex array of factors encoded by both the chromosome and three plasmids, including the Lcr genes, a fibrinolysin and a capsule.

Man is an occasional host in the natural cycle of the disease, and bubonic plague, characterised by the swelling of local lymph nodes, may occur following the bite of an infected flea. One of the complications of bubonic plague is secondary pneumonia, and in these cases the disease is readily transmitted between humans by airborne droplets. Plague is endemic in regions of North and South America, Africa, China and Asia (see Butler (1983) Plague and Other Yersinia Infections; Plenum Press, New York). Current outbreaks are believed to be part of the fourth world pandemic of the disease, with a clear need to protect individuals living or travelling in endemic areas, and laboratory workers handling the bacterium.

The current whole cell vaccines available for prevention of plague are highly heterogeneous. resulting in side effects which make them unsuitable for widespread use (eg Meyer et al (1974) J. Infect Dis 129 supp 13–18 and 85–120: Marshall et al (1974) ibid supp 19–25).

One current vaccine for plague is the Cutter vaccine which comprises formaldehyde killed plague bacilli and is administered to the body by intramuscular injection. However, parenteral immunisation, although effective in inducing systemic immunity, does not effectively induce mucosal immunity (McGhee et al, (1992) Vaccine 10, 75–88) and cases of pneumonic plague have been reported in vaccinated individuals (Meyer (1970) Bull WHO 42 p663-668). So far no vaccine capable of producing a protective immune response at mucosal surfaces has been reported.

The live attenuated EV76 vaccine was tested extensively and used in the former Soviet Union from 1939, although its efficacy in evoking an immune response in man is questionable (Meyer et al (1974) J. Infect. Dis. 129 Supp: 13–18). It has been shown that the virulence of EV76 differs in several animal species. and non-human primates are particularly susceptible to a chronic infection with this strain. In the Western World the vaccine is considered to be unsuitable for mass vaccinations due to the extreme severity of the side effects and the possibility of the strain reverting to full virulence.

Two known *Y. pestis* antigens are the *Y. pestis* LcrV (V antigen), and the F1 antigen: both of which have now been found to be capable of evoking protective immune responses in animals. The present inventors have previously provided live orally active vaccine microorganisms capable of expressing V antigen and F1 antigen respectively which each provide good protection against challenge with *Y. pestis* at up to $10^3$ cfu. These vaccines are the subject of copending patent applications PCTIGB94/02818 and GB 9404577.0.

The present inventors have now surprisingly found that whereas only the unacceptably hazardous EV live vaccine had been shown to be capable of giving good protection against challenge with $10^9$ cfu or more with *Y. pestis* GB strain, and V and F1 antigens alone only provide full protection against challenge with about $10^5$ cfu. by administering a combined vaccine comprising V and F1 antigens they can at least match the protection afforded by EV76 without any of the hazards that have kept the EV vaccine from general use.

Still more advantageously, they have found that the vehicle for administration may be a simple mixture of the two protein components, rather than as a more complex attenuated whole organism. For long term protection and for the purposes of producing mucosal immunity, they have provided preferred forms of vaccine compnsing the two components in the form of live attenuated vaccine such as the F1 and V expressing Aro A or C *Salmonella typhi* referred to in the aforesaid copending applications, and in more preferred forms a single or double mutant expressing these antigens separately, or a fusion protein comprising both antigens.

Further provided are micro-organisms comprising both of F1 and V types of construct or plasmids of the applicants copending applications referred to above. These contain constructs that are capable of transforming a human or animal gut colonising micro-organism such that it is enabled to express proteins that are equivalent in sequence to F1 and V antigens respectively; these producing a protective immune response against *Yersinia pestis* in a human or animal body when the micro-organism is administered by oral or parenteral routes, and preferably allow the micro-organism to maintain its ability to colonise the human or animal gut.

A particularly preferred recombinant DNA, plasmid or human or animal gut colonising organism encodes for or expresses all or a protective epitopic part of the mature V protein of *Yersinia pestis* and all or a protective epitopic part of the mature F1 protein of *Yersinia pestis*. DNA encoding the whole or part of the F1 antigen and DNA encoding the whole or part of the V antigen could be used directly as a genetic vaccine.

Particularly preferred recombinant DNA encoding for V comprises a DNA sequence as described in SEQ ID No 1 or SEQ ID No 3, more preferably positioned in frame with a promoter such as lacz or nirβ, and preferably in a vector capable of expression and replication in a Salmonella. Particularly preferred recombinant DNA encoding for F1 comprises a DNA sequence as described in SEQ ID No 10. SEQ ID No 2 and SEQ ID No 4 show the amino acid sequences of two preferred V antigen proteins; SEQ ID No 2 being the sequence of the V-antigen itself, and SEQ ID No 4 being that of V-antigen with four extra vector defined N-terminal amino acids. SEQ ID No 11 is that of an F1 protein as encoded for by SEQ ID No 10.

The preferred DNA constructs used in microorganisms of the invention allow production of micro-organisms that when orally administered induce local stimulation of the gut-associated lymphoid tissue (GALT) and, by trafficking of lymphocytes through the common mucosal immune system provide a secondary stimulation of the bronchial associated lymphoid tissue (BALT). In this manner a secretory IgA response is achieved at the respiratory mucosal surface.

The micro-organisms provided by transformation using this DNA in vector or directly inserted format, are preferably attenuated, more preferably attenuated salmonella.

Attenuated micro-organisms such as *S. typhimurium* have been well characterised as carriers for various heterologous antigens (Curtiss, (1990); Cardenas and Clements, (1992)). Attenuation may be effected in a number of ways, such as by use of the aro A and/or aro C mutation approach (see Hosieth et al (1981) Nature 291. 238–239: Dougan et al (1986) Parasite Immunol 9, 151–160; Chatfield et al (1989) Vaccine 7, 495498); multiple mutations such as aro A and aro C mutants as described by Hone et al (1991) Vaccine 9, pp 810–816 may also be used. However, any suitably defective organism that is safe for intended use may be employed.

Many other such attenuated deletions and mutations will be known for these and other microorganisms which will render them suitable for transformation with constructs of the present invention for the purposes of expressing vaccine proteins in the gut and/or gut colonisation in animals to be treated for Y.pestis. For human vaccination vectors containing the constructs of the present invention are placed in attenuated S. typhi and that transformed organism used as active agent for a live oral vaccine.

When DNA is used to transform the attenuated microorganism by direct insertion into microorganism DNA this may be by direct integration into a gene. Alternatively when incorporated in the form of a plasmid that expresses V or F1 protein or epitopic fragments thereof this may be such that only the V or F1 protein or fragment is expressed or that this is expressed as a fusion peptide with a further protein or peptide fragment, preferably including the other one of the antigenic F1/V components. Such further protein or peptide fragment might be such as to promote export of mature proteins or peptide through the cell membrane or might be a further Y. pestis antigen.

The Icr gene was cloned from Y. pestis strain KIM by Price et al and its nucleotide sequence published in J Bacteriol (1989) 171, pp 5646–5653. In the examples below this information was used to design oligonucleotide primers which could amplify the gene from Y. pestis (strain GS) using the polymerase chain reaction (PCR). PCR primers were designed to be complementary to respective sequences flanking the 5' and 3' ends of the Icrv gene but also having 5' end tails containing a restriction enzyme recognition site to enable amplified IcrV gene to be cloned directionally into a plasmid vector (the 5' PCR primer containing an EcorRI site and the 3' primer containing a SacI site). These restriction enzyme sites are examples only and should not be seen as excluding other restriction enzymes.

In the examples below the constructs of the invention include a lac promoter, but other promoters such as the macrophage promoter (nirβ) may be used.

The production of Fl has been described fully in Oyston et al (1995) Infect. Immun. Vol. 63 No 2 p563 - see page 564 under results: Cloning and Expression of caf1.

The dosage of the antigen components in a vaccine may vary dependent upon an individual animals immune characteristics, but for immunisation in the mouse animal model of the examples below it has been found that 10 $\mu$g of each of V and F1 per dose were effective in providing full protection when administered in a standard primer and booster schedule.

The antigens may be incorporated into a conventional pharmaceutically acceptable carrier, no particular limitation being imposed here. Conveniently the antigens have been incorporated into an oil in water emulsion. Adjuvants may be included in the vaccine composition, and particularly Freund's Incomplete adjuvant IFA has been found to be effective when treating the mouse model.

The carrier may be one suited to parenteral administration, particularly intraperitoneal administration but optionally oral, in the case of micro-organism based vaccines, or administration in the form of droplets or capsules, such as liposomes or microcapsules as would be effective in delivering the composition to the airways of an individual for the purpose of evoking mucosal immune response. The carrier may also comprise a slow-depot release system e.g. Alhydrogel.

Another method of encapsulation includes the use of polymeric structures in particular linear block co-polymers. Biodegradable polymers for example poly-lactic acid with or without glycolic acid or block co-polymer may be used; these may contain the following repeat unit: (POP-POE)$_n$ where POP is polyoxypropylene and POE is polyoxyethylene. Block copolymers which contain (POP-POE)$_n$ are of particular use.

The method, constructs, micro-organisms and vaccines of the invention will now be exemplified by way of illustration only by reference to the following Sequence using Figure and Examples. Still further embodiments will be evident to those skilled in the art in the light of these.

SEQUENCE LISTING

Figure 1:
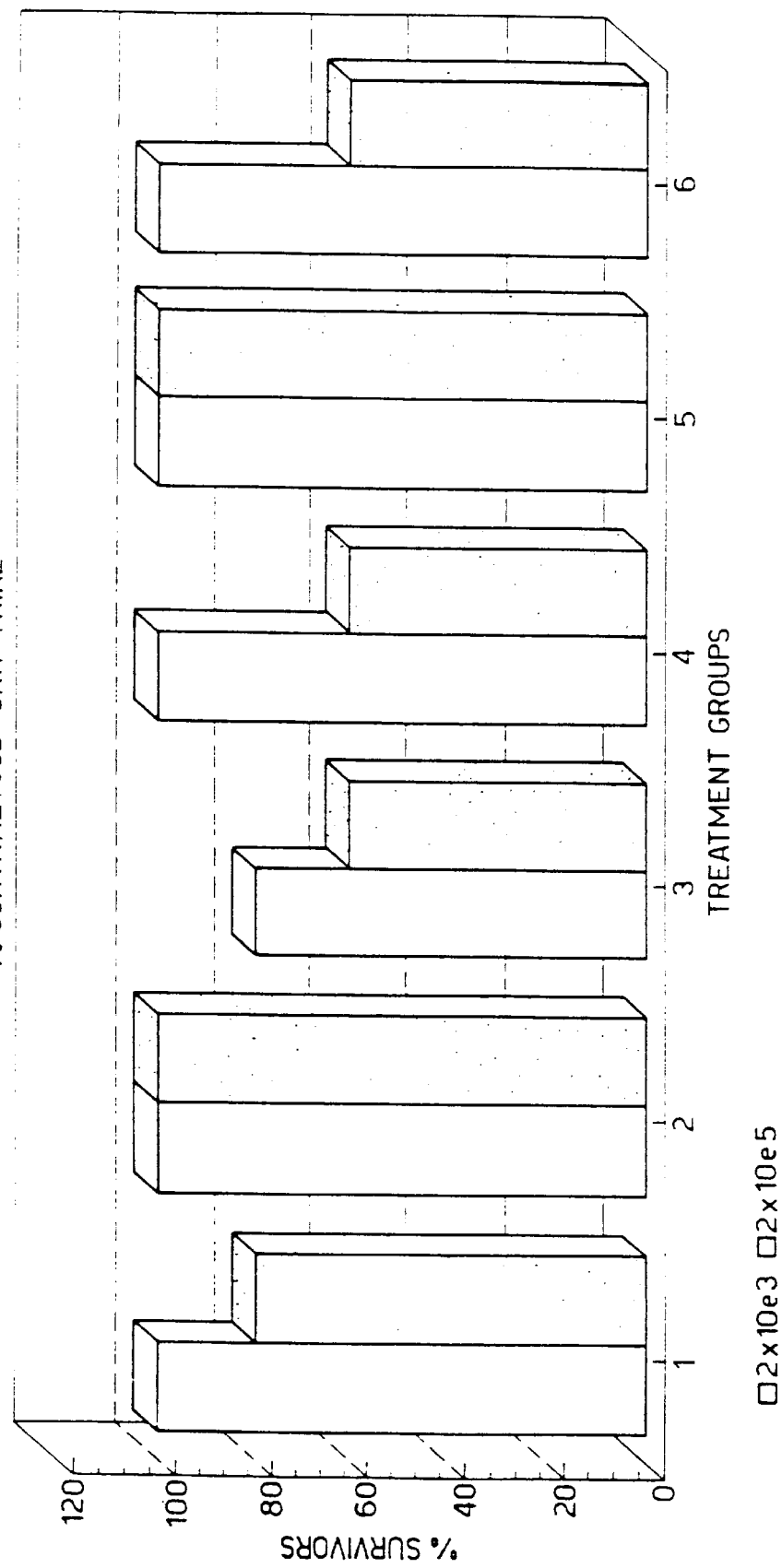
FIG. 1 illustrates in bar-chart form the survival rates of a number of groups against a challenge of Y.pestis.

SEQ ID No 1: Shows the nucleotide and derived amino acid sequence of a V-encoding DNA with 6 bases of vector pMAL-p2 or pMAL-c2 into which it is cloned at the 5' end using the EcoRI site in sequence GAATTC (derived from the 5' end PCR primer) and at the 3' end at the SalI site in sequence GTCGAC (derived from the 3' end PCR primer). The base at position 1006 has been altered by PCR mutagenesis to a T to create a second in frame stop codon. The start of the amino acid sequence is C-terminal to a factor Xa cleavage site.

SEQ ID No 2: Shows the amino acid sequence of the peptide expressed by the insert DNA of the invention, with an additional four amino acids encoded for by the vector (IE+FS) at the N-terminal end.

SEQ ID No 3: Shows the nucleotide and derived amino acid sequence of a second V-encoding DNA of the invention with 10 bases of a vector pGEX-5X-2 into which it is cloned shown at the 5' end using the EcoRl site in sequence GAATTC (GA derived from the 5' end PCR primer) and the SalI site in sequence GTCGAC (GTCGAC derived from the 3' end PCR primer). The base at position 1006 has been altered by PCR mutagenesis to create a second in frame stop codon; the base at position 16 has been altered to a C from an A to create the EcoRI site. The start of the amino acid sequence is C-terminal to a factor Xa cleavage site.

SEQ ID No 4: Shows the amino acid sequence of the peptide expressed by the DNA of SEQ ID No 3, with four amino acids encoded by the vector (G, I, P and G) at the N-terminal end.

SEQ ID No 5: Shows the nucleotide sequence of a gene 5' end primer oligonucleobde used to generate V-encoding DNA used in SEQ ID No 1.

SEQ ID No 6: Shows the nucleotide sequence of a gene 3' end primer oligonucleotide used to generate V-encoding DNA used in the Examples.

SEQ ID No 7: Shows the nucleotide sequence of a PCR primer oligonucleotide corresponding to the first 21 bases encoding for mature caf1 with an additional 5' region encoding for a SacI site.

SEQ ID No 8: Shows the nucleotide sequence of a PCR primer oligonucleotide corresponding to the sequence of caf1 which encodes a 'stem loop' downstream of the termination codon with an added 5' region encoding SacI and AccI sites.

SEQ ID No 9: Shows the nucleotide sequence of a PCR primer oligonucleotide corresponding to an internal end region of the caf1 gene starting 107 bases downstream from the end of the first oligonucleotide.

SEQ ID No 10: Shows the nucleotide sequence of the pFGAL2a construct showing the fusion of the first few bases of the β-galactosidase sequence in the vector with caf1 minus its signal sequence and having a 5' tail including a Sac I restriction site: the sequence is shown up to the caf1 AACC 3' end with some vector bases.

SEQ ID No 11: Shows the amino acid sequence of the protein encoded by OFGAL2a. This sequence may be proceeded by Met, Thr, Met, lie, Thr. Asn.

SEQ ID No 12: is that of primer FIOU2 used to amplify the F1 operon.

SEQ ID No 13: is that of primer M4D used to amplify the F1 operon.

SEQ ID No 14: is that of primer M3U used to amplify the F1 operon.

SEQ ID No 15: is that of primer FIOD2 used to amplify the F1 operon.

SEQ ID No 16: is the nucleotide and derived amino acid sequence of a DNA fragment encoding an F1-V fusion protein. There is a SacI cloning site at the 5' end and a Hind III cloning site at the 3' end. Bases 452–472 is a sequence contained in the cloned insert, but derived from PCR primers (not found in Y. pestis DNA).

SEQ ID No 17: is the amino acid sequence of SEQ ID No 16.

SEQ ID No 18: is that of primer 5'FAB2 used to amplify the F1 operon including signal sequence.

SEQ ID No 19: is that of primer 3'FBAM used to amplify the F1 operon including signal sequence.

SEQ ID No 20: is the nucleotide and amino acid sequence for F1 antigen as defined by PCR primers detailed in exemplified SEQ ID No 18 and 19 including signal sequence.

SEQ ID No 21: is the amino acid sequence of SEQ ID No 20.

SEQ ID No 22: is the nucleotide and amino acid sequence of F1/V fusion protein including a 5 amino acid linker region. The T at position 1522 was modified from G to create a second in frame stop codon.

SEQ ID No 23: is the amino acid sequence of SEQ ID No 22. The linker region referred to in SEQ ID No 22 is at amino acid position 171–176 (bases 523–540 in SEQ. ID No 22).

SEQ ID No 24: shows the nucleotide sequence of a gene 5' end primer oligonucleotide used to generate V-encoding DNA used in SEQ ID No 3.

EXAMPLES

Cloning of SEQ. ID No 3

Materials and Methods: Materials for the preparation of growth media were obtained from Oxoid Ltd. or Difco Laboratories. All enzymes used in the manipulation of DNA were obtained from Boehringer Mannheim UK Ltd. and used according to the manufacturer's instructions. All other chemicals and biochemicals were obtained from Sigma chemical Co unless otherwise indicated. Monospecific rabbit polyclonal anti-V and mouse anti-GST sera were prepared by Dr R Brubaker (Department of Microbiology, Michigan State University) and Dr E D Williamson (Chemical and Biological Defence Establishment), respectively.

Bacterial strains and cultivation: Yersinia pestis GB was cultured aerobically at 28° C. in a liquid medium (pH 6.8) containing 15 g proteose peptone, 2.5 g liver digest. 5 g yeast extract. 5 g NaCl per liter supplemented with 80 ml of 0.25% haemin dissolved in 0.1M NaOH (Blood Base Broth). Escherichia coli JM109 was cultured and stored as described by Sambrook et al. Molecular Cloning. A Laboratory Manual.

Production of recombinant V and F1 proteins: Manipulation of DNA. Chromosomal DNA was isolated from Y. pestis by the method of Marmur.

Production of recombinant V-antigen: The gene encoding V-antigen (1crV) was amplified from Y. pestis DNA using the polymerase chain reaction (PCR) with 125pmoi of primers homologous to sequences from the 5' and 3' ends of the gene (see Price et al (1989). J. Bacteriol 171 p5646–5653).

The sequences of the 5' primer (V/5'E: GATCGAATTCGAGCCTACGAACAA) and the 3' primer (GGATCGTCGACTTACATAATTACCTCGTGTCA) also included 5' regions encoding the restriction sites EcoR1 and Sal1, respectively. In addition, two nucleotides were altered from the published sequence of IcrV (Price et al, 1989), so that the EcoRI site was completed and the amplified gene encoded an extra termination codon (TAA). The PCR pnmers were prepared with a DNA synthesiser (392 Applied Biosystems) Applied Biosystems. A DNA fragment was obtained after 30 cycles of amplification (95° C., 20secs, 45° C., 20 secs, 72° C. 30 secs: Perkin 9600 GeneAmo PCR System). The fragment was purified, digested with EcoR1 and Sal1. ligated with suitably digested plasmid pGEX-5X-2 and transformed into E. coli JM109 by electroporation (see Sambrook et al 1989). A colony containing the recombinant plasmid (pVG 100) was identified by PCR using 30-mer primers (5' nucleotides located at positions 54 and 794: see Price et al 1989) which amplified an internal segment of the IcrV gene.

Expression of rV in E. coli. Cultures of E. coli JM109/pVG100 were grown in LB containing 100 $\mu$gml$^{-1}$ ampicillin at 37° C. until the absorbance (600 nm) was 0.3. Isopropyl-β-D-thiogalactopyranoside (IPTG) was then added to the culture to a final concentration of 1 mM and growth was continued for a further 5 hours. Whole cell lysates of the bacteria were prepared as described in Sambrook et al and expression of the GSTN fusion protein was examined by staining 10% SDS-polyacrylamide gels (Mini-Protean II, BioRad) with Coomassie Brilliant Blue R250 and by Western Blotting (see Sambrook et al). Western Blots were probed with rabbit anti-V serum diluted 1/4000 or mouse anti-GST serum in dilution at 1/1000 and protein bands were visualised with a colloidal gold labelled secondary antibody (Auroprobe BLplus, Cambio).

Quantification of GSTN expression in vitro. Cultures of E. coli JM109 containing pVG1OO or pGEX-5X-2 were grown as described above. One ml aliquots were removed from the cultures in logarithmic and stationary phases and the number of viable cells determined by inoculating onto L-agar containing ampicillin. The cells were harvested from a second 1 ml aliquot by centrifugation and resuspended in 1 ml of phosphate buffered saline (PBS). The cell suspension was frozen at −20° C. for 1 hour, thawed and then sonicated on ice at 10° C. lower for 3×30 secs (model XL2015 sonicator, 3.2 mm Microtip probe; Heat Systems Inc.). The sonicates and a standard solution of rV (5ugml$^{-1}$) were serially diluted in PBS in a microtitre plate and allowed to bind overnight at 4° C. The quantity of GST/V fusion protein in each sonicate was determined in a standard ELISA using rabbit anti. V serum as the primary antibody. Antibodies were incubated in 1% skimmed milk powder in PBS.

Purification of rV. *E. coii* JM109/pVG100 was grown in 5×100 ml volumes of LB as described above. The cells were harvested by centrifugation ana resuspended in 3 ml. phosphate buffered saline (PBS). After the addition of 80 μl lysozyme (10 mgml$^{-1}$; the cell suspension was incubated for 10 min at 22° C. Triton X-100 was added to final concentration of 1% and the cells were frozen (−20° C.), thawed and sonicated on ice at 70%, power for 3×30 s (model XL2015 sonicator). The lysed cells were centrifuged, and the supernatant was made up to 30 ml with PBS and mixed with 5 ml of Glutathione Sepaharose 4B (Pharmacia Biotech) which had been washed three times with PBS+ 0.1% Triton X-100. The mixture was stirred for 18 hours at 4° C., centrifuged and washed twice in 100 ml PBS. and then packed into a chromatography column (Poly-Prep: Bio-rad) as a 50% slurry. The GST/V fusion protein was eluted with 10 ml of 50 mM Tris pH 8.0 containing 5 mM reduced glutathione (Pharmacia Biotech). After dialysis against PBS, the fusion protein was cleaved with factor Xa (Boehringer Mannheim UK Ltd) for 18 hours at 22° C., according to the manufacturer's instructions. Cleaved GST and excess uncleaved GSTN were removed from the solution by affinity adsorption, as described above, to leave purified recombinant V (rV).

Immunisation with rV. Six week old female Balb/c mice, raised under specific pathogen-free conditions (Charles. River Laboratories, Margate, Kent. UK), were used in this study. A group of 16 mice received a 0.2 ml primary immunising dose intraperitoneally (i.p.) of 10.13 μg of rV antigen, presented in a 1:1 water-in-oil emulsion with Incomplete Freund's Adjuvant (IFA). On days 14 and 34, each animal received booster immunising doses, prepared as above. On day 64, 6 animals were sacrificed and their tissues were removed for immunological analyses. as described below. The remaining animals were challenged with *Y. pestis*. An untreated control group of 16 age-matched mice were divided similarly into groups for tissue sampling and challenge. In a subsequent experiment to determine the degree of protection against higher challenge doses of *Y pestis* groups of 5 or 6 rV-immunised and control mice were used.

Measurement of serum antibody titre. Blood was sampled by cardiac puncture from mice anaesthetised i.p. with a 0.1 ml cocktail containing 6 mg of Domitor (Norden Laboratories) and 27 μg cf Ketalar (Parke-Davies). The samples were pooled and the serum was separated. The serum antibody titre was measured by a modified ELISA (Willamson and Tiball, (1993) Vaccine 11: 1253–1258). Briefly, rV (5 μgml$^{-1}$ in PBS) was coated onto a microtitre plate and the test sera were serially diluted in duplicate on the plate. Bound antibody was detected using peroxidase labelled conjugates of anti-mouse polyvalent 1 g. The titre of specific antibody was estimated as the maximum dilution of serum giving an absorbance reading greater than 0.1 units. after subtraction of the absorbance due to non-specific binding detected in the control sera.

Isolation of purified T cells from the spleen. A crude suspension of mixed spleen cells was prepared by gently grinding the spleen on a fine wire mesh. The cells were flushed from the splenic capsule and connective tissue with 2 ml of tissue culture medium (DMEM with 20 mM L-glutamine, 10$^5$U1$^{-1}$ of penicillin and 100 mgl$^{-1}$ of strepomycin). A population of mixed lymphocytes was separated from the spleen cell suspension by density gradient centrifugation of Ficoll-Hypaque (Lymphocyte Separation Medium, ICN Flow). A mixed acridine orange (0.0003% w/v) and ethidium bromide (0.001% w/v) stain was used to determine the percentage of viable cells in the preparation.

The mixed lymphocytes were incubated with sheep anti-mouse IgG-coated Dynabeads (M450), Dynal UK) at a ratio of 1:3 for 30 minutes at 4° C. The Dynabead linked B cells were removed by magnetic separation and the remaining T cells were resuspended in DMEM, supplemented with antibiotic and 10% v/v foetal calf serum (FCS) at the desired cell density for seeding to microtitre plates.

In vitro proliferation of crude spleen cells and purified T cells against rV. Doubling dilutions of rV or Concanavalin A (positive control) in DMEM (range 0–50 μgml$^{-1}$) were made in the wells of a microtitre plate, such that 0.1 ml remained in each well. Negative controls consisted of 0.1 ml of DMEM alone. An equal volume of the crude spleen cell or purified T cell suspension was seeded into each well at a minimum density of 5×10$^4$ cells and incubated for 72 hours at 37° C. (5% CO$_2$). One μCi of $^3$H thymidine ([methyl[$^3$H] thymidine S.A. 74 GBqmmol$^{-1}$; Amersham) in 30 μl of DMEM supplemented with 10% FCS was aliquoted into each well and incubation was continued for 24 h. The well contents were harvested onto glass fibre filters using a cell harvester (Titertek) and discs representing each well were punched from the filter mats into 1.5 ml of scintillation fluid (Cyoscint. ICN Biomedicals Inc.) so measure the incorporation of $^3$H thymidine into cells. The cell stimulation index was calculated from a replicates as mean cpm (stimulated)/mean cpm (negative control).

Production of recombinant F1 antigen. Cloning of caf1: DNA was isolated from *Y. pestis* by the method of Marmur et al (1961) J. Mol. Biol. 3: pp 208–218. A DNA fragment encoding the open reading frame of caf1 minus its signal sequence was amplified from this using the polymerase chain reaction (PCR). Oligonucleotides were prepared with a Beckman 200A DNA synthesiser for use in the PCR.

pFGAL2a construct. Oligonucleotide GATCGAGCTCGGCAGA7T'AACTGCAAGCACC (SEQ ID No 7) was synthesised corresponding to the first 21 bases of the caf1 gene immediately following the nucleotides encoding the signal sequence with an additional 5'region encoding a SacI site and the complimentary oligonucleotide CAGGTCGAGCTCGTCGACGGTTAGGCTCAAAGTAG (SEQ ID No 8) corresponding to the sequence which encodes a putative 'stem loop' structure downstream of the caf1 termination codon with an added 5'region encoding SacI and AccI sites. A DNA fragment was obtained after 35 cycles of amplification (95° C., 15 secs; 50° C., 15 secs; 72° C., 30 secs using a Perkin Elmer 9600 GeneAmp PCR system). The fragment was purified, digested with SacI and AccI, ligated into a similarly digested pUC18 plasmid and transformed into *E. coli* JM109 by electroporation. Electroporation was carried out using a Biorad Gene Pulser with 0.2 cm cuvettes at 1.25kV. 25pF, 800 Ohms with a time constant of 20.

A pFGAL2a colony containing the cloned caf1 gene was identified by PCR using an oligonucleotide TGGTACGCT-TACTCTTGGCGGCTAT (SEQ ID No 9) corresponding to an internal region of the gene 128 to 153 nucieotides from the site identified as the signal sequence cleavage site (see Galyov et al (1990)) and the SEQ ID No 2. An F1 expressing *E. coli* culture containing the pFGAL2a was grown at 37° C. with shaking in Luria Broth with 1 mM isopropyl-β-D-thiogalactopyranoside (IPTG) for 18 hours. Whole cell lysates and periplasmic and cytoplasmic fractions of the bacteria were prepared as described by Sambrook et al (1989).

SDS-PAGE and Western blotting: SDS-polyacrylamide gel electrophoresis (PAGE) and Western blotting were performed as described by Hunter et al (1993) Infec. Immun. 61. 3958–3965. Blots were probed with polyclonal antisera raised in sheep (B283) against killed *Y pestis* (EV76 strain grown at 37° C.) and bound antibody was detected with a horseradish peroxidase-labelled donkey anti-sheep IgG (Sigma).

Examples 1 and 2 of Combination V/F1 Vaccine, Comparative Examples, Effects of Vaccines on Mortality of Mice on Challenge with *Y. pestis* (GB) Strain Animals: Barrier bred female 6-week old Balb/c mice free of mouse pathogens were obtained from Charles-Reiver Laboratories, Margate. Kent. UK and were used throughout these Examples.

Immunisation: Mice were divided into groups of 5 or 6 and immunised as follows.

Comparative vaccine EV76: A total of 50 mice received a single subcutaneous (s.c.) priming dose of live EV76 vaccine on day 0 of the schedule delivered in a total volume of 100 µl.

Comparative vaccine Cutter USP vaccine: A further group of 50 mice were primed intramuscularly (i.m.) with 100 µl of Cutter vaccine; this representing about 0.2 of the human dose and comprised approximately $2 \times 10^8$ formaldehyde killed plague bacilli. This dose was administered to each animal again on day 16 of the schedule to effect booster immunisation.

F1 and V vaccines: Groups of 62 mice received a primary immunising dose intra-peritoneally (i.p.) of either recombinant V-antigen or recombinant F1-antigen, presented in a 1:1 water-in-oil emulsion with incomplete Freunds adjuvant (IFA; Sigma). Animals were primed with a 18 µg dose of the respective antigen in a total volume of 0.1 ml emulsion. Animals were boosted with the respective antigen as appropriate on days 14 (V and F1 groups) and 28 (all F1 group and a subgroup of 12 of the V group).

A further group of 12 mice were primed and boosted on days 0. 14 and 28 with a combination of 10 µg F1 and 10 µg V jointly incorporated into the aqueous phase of a 1:1 water-in-oil emulsion with IFA (final volume 0.1 ml per mouse).

On day 50 of the immunisation schedule, 6 animals were selected at random from each of the treatment groups for subsequent analysis of spleen cell responses. The remaining animals in each group were challenged with *Y. pestis*. An untreated control group of age-matched mice was similarly split.

Multiple LD challenge to determine limits of protection: Mice from each of the immunised groups and untreated controls were divided into groups of 5 or 6 for challenge by the s.c. route with *Y. pestis* GB strain in the dose range 20 to $2 \times 10^9$ viable organisms. Challenged mice were closely observed over a 14-day period for the development of symptoms and where appropriate time to death was carefully recorded.

Animals which succumbed to the challenge were autopsied and blood smears, livers and spleens removed for bacteriological analysis.

The results of these challenges on control and test animals is given in Table 1 below; two sets of results being given corresponding two experimental runs with respective controls. From these results it can clearly be seen that while the V antigen is more effective than Cutter, it is inferior to EV76. However, when combined with the less effective F1 the combination is as effective as EV76 without side effects.

TABLE 1

| VACCINE | GB CHALLENGE (cfu) | SURVIVORS | MEAN TTD (hr ± sem) | SKIN LESIONS | SICK |
|---|---|---|---|---|---|
| Set 1 results | | | | | |
| EV | $2 \times 10^9$ | 5/5 | | + | − |
| EV | $2 \times 10^8$ | 4/5 | | + | − |
| EV | $2 \times 10^7$ | 6/6 | | + | − |
| EV | $2 \times 10^6$ | 6/6 | | + | − |
| EV | $2 \times 10^5$ | 6/6 | | + | − |
| Cutter | $2 \times 10^9$ | 0/5 | 119 ± zero | + | − |
| Cutter | $2 \times 10^8$ | 0/5 | 171 ± 11.63 | + | + |
| Cutter | $2 \times 10^7$ | 1/5 | 160 ± zero | + | + |
| Cutter | $2 \times 10^6$ | 3/5 | 120 ± 8.49 | + | + |
| V | $2 \times 10^9$ | 0/5 | 102.4 ± 21.4 | + | + |
| V | $2 \times 10^8$ | 4/5 | 156 ± zero | − | − |
| V | $2 \times 10^7$ | 5/5 | | − | − |
| V | $2 \times 10^6$ | 4/5 | 64 ± zero | − | − |
| V | $2 \times 10^5$ | 4/5 | 112 ± zero | − | − |
| Control | $2 \times 10^9$ | 0/5 | 64 ± zero | − | + |
| Control | $2 \times 10^4$ | 0/5 | 121.6 ± 16.06 | − | + |

TABLE 2

| VACCINE | GB CHALLENGE (cfu) | SURVIVORS | MEAN TTD (hr ± sem) | SKIN LESIONS | SICK |
|---|---|---|---|---|---|
| Set 2 results | | | | | |
| F1 | $2 \times 10^9$ | 0/5 | 98.6 ± 8.41 | − | + |
| F1 | $2 \times 10^7$ | 3/5 | 124 ± 8.49 | − | + |
| F1 | $2 \times 10^5$ | 4/5 | 136 ± zero | − | +/− |
| F1 | $2 \times 10^3$ | 5/5 | | − | − |
| F1 | 20 | 5/5 | | − | − |
| V | $2 \times 10^9$ | 0/5 | 102.4 ± 8.59 | − | + |
| V | $2 \times 10^5$ | 5/5 | | − | − |
| F1 + V* | $2 \times 10^9$ | 5/5 | | − | − |
| F1 + V** | $2 \times 10^5$ | 5/5 | | − | − |
| Control | $2 \times 10^9$ | 0/5 | 64 ± zero | − | + |

\* = Example 1
\*\* = Example 2

Example 3.

Production of Attenuated Salmonella for use in oral vaccine.

Expression of recombinant V-antigen from *S. typhimurium* and *typhi*.

Amplified IcrV gene was cloned into three different plasmid vectors:

pMAL-p2: a vector designed to express the cloned gene as a fusion product with a maltose binding protein (MBP). The C-terminus of the MBP is fused to the N-terminus of the V-antigen. The fusion protein so produced on expression is exported to the periplasm. Vector including the V-antigen DNA sequence was designated pVMP100.

pMALC2: a vector similar to pMAL-p2 except that MBP-V antigen fusion protein is expressed cytoplasmically. The recombinant plasmid was designated pVMC100.

pGEX-5X-2: a vector designed to express the cloned gene as a fusion protein with glutathione-S-transferase (GST). The C-terminus of GST is fused to the N-terminus of V antigen and the fusion protein is expressed cytoplasmically. The recombinant plasmid was designated pVG100.

All the vectors contain the $P_{tac}$ promoter and the $lacI^Q$ gene: the latter encoding the lac repressor which turns off transcription from $P_{tac}$ in *Escherichia coli* until IPTG is added. The plasmids contain the origin of replication from pBR322 and as a result replicate to a low copy number in the bacterial cell.

Each of the recombinant plasmids was electroporated into *Salmonella typhimurium* strain SL3261, an attenuated strain that has been used extensively as a live vaccine vector for the expression of foreign antigens. It contains a specific deletion mutation in the aroA gene which makes the mutant dependent upon certain aromatics for growth (see Hosieth et al). For producing microorganism suitable for human vaccination use electroporation is into attenuated *Salmonella typhi*.

The recombinant plasmids all expressed V antigen as shown by Western blotting of *S. typhimurium* cultures and probing with a monospecific anti-V antigen polyclonal antiserum supplied by R Brubaker, Dept Microbiology, Michigan State University, East Lansing, Mich. 48824-1101, USA. Recombinant *S. typhimurium* were innoculated intravenously into mice at $5 \times 10^7$ cfu/dose and shown to colonise the liver and spleen at high levels: between $8 \times 10^6$ and $5 \times 10^8$ cfu per organ were recovered. The majority of the bacterial cells recovered were also ampicillin resistant indicating retention of recombinant plasmids.

Expression of F1 in *S. typhimurium:* The pFGAL2a plasmid was isolated using general techniques described in Sambrook et al (1989) Molecular Cloning; a Laboratory Manual, 2nd Edition. Cold Spnng Harbour Laboratory, New York. Purified plasmid was electroporated into *S. typhimurium* LB5010 (restriction, modification) and methylated pFGAL2a was subsequently isolated from the LB5010 for electroporation into *S. typhimurium* SL3261 (aro A). Peeplasmic and cyptoplasmic fractions were prepared for SDS-PAGE and Western blotting as described above.

Stability of constructs: Five female Balbic mice were inoculated intravenously with either $5 \times 10^5$ or $5 \times 10^7$ cfu *S. typhimunum* containing pFGAL2a in 200 μL phosphate buffered saline. Control mice were inoculated similarly with *S. typhimurium* containing pUC18 with no insert. After 7 days the mice were killed by cervical dislocation and their livers and spleens removed. The organs were homogenised in 10 ml phosphate buffered saline using a stomacher on maximum setting for 2 minutes and the homogenate was serially diluted in phosphate buffered saline and placed onto L agar or L agar containing 55 μg ml$^{-1}$ ampicillin.

F1 operon construct: Attempts to PCR replicate the entire F1 operon as one piece were unsuccessful, so a strategy was developed whereby it was amplified using PCR to produce two discrete fragments using primer pairs (A) of SEQ ID No 12 and 13 and (b) of SEQ No 14 and 15 respectively to produce fragments of 3.36 kb and 1.89 kb from *Y. pestis* MP6 template DNA. Marmur extract of DNA was used without $CsCl_2$ purification. The PCR cycle conditions used were 96° C. for 30 seconds, 57° C. for 30 seconds and 72° C. for 1 minute; total of 30 cycles.

These two fragments were digested using Nhe1 and joined together.

This fused fragment, encoding the full length operon (5.25kb), was digested with EcoR1 and Sal1 and then cloned into a number of vectors. When this fragment was cloned into pBR322 and expressed in *E. coli, S. typhimudum* LBE5010 or SL3261 instability of the recombinant plasmid was noted. To circumvent this problem the operon was cloned into plasmid pLG339, a low copy number plasmid km$^R$. The entire F1 operon was also inserted into AroC gene on the chromosome of gene on the chromosome of *S. typhimurium* using vector pBRD1084.

As discussed previously in this application. the V and F1 antigen may be microencapsulated. The V and F1 antigens may be separately microencapsulated. The combined microencapsulated sub-units may be used for immunisation. The present inventors believe that the protection afforded by the combined microencapsulated sub-units is superior to that provided by existing plague vaccines and that there is an additive effect in combining the sub-units. The protective efficacy of the combined microencapsulated sub-un-its may further be enhanced by co-administering an adjuvant for example cholera toxin B sub-unit (CTS). Microencapsulation of the sub-unit vaccine prolongs release of the vaccine in vivo. permits oral. intra-nasal or inhalational delivery and gives scope for targetting.

The microencapsulation of the combined V and F1 sub-unit vaccine is described below. Also demonstrated is that this formulation is able to induce both mucosal and systemic immunity against plague.

The microencapsulation of sub-units was effected in PLA 2000 using a solvent evaporation technique.

Immunisation with the microencapsulated sub-units was carried out as follows.

Groups of 21 mice received a primary immunising dose of 25 μg of either V antigen or F1 antigen, presented in microspheres resuspended in PBS for intra-peritoneal (i.p.) injection. Further groups of 21 mice received a combination of 25 μg of each of the F1 and V antigens, presented in microspheres. A dose of 25 μg of F1 was delivered in a total mass of 5.42 mg of spheres, whilst 25 μg of V was contained in 2.08 mg of spheres. The required mass of microspheres was re-suspended in 100 μl PBS per animal for injection. Animals were boosted with the respective antigen(s), as appropriate on days 14 and 28.

Two further groups of 21 mice were primed and then boosted i.p. on days 14 and 28 with a combination of 10 μg F1 and 10 μg V. jointly incorporated in the aqueous phase of 25% (v/v) suspension of alhydrogel (Alhydrogel 1.3%, Superfos. Denmark) in PBS Selected groups of animals received in addition a dose of 10 μg CTB (Sigma, Poole) incorcorated into the delivery vehicle at each dosing point.

Control groups, each of 21 mice, received either alhydrogel only (100 μl of 25% solution) or CTB only (10 μg in 100 μl PBS) or remained untreated.

In order to compare the protective efficacy of immunisation with combined sub-units, free or microencapsulated, against that provided by the Greer vaccine, (purchased from Greer laboratories) animals were challenged s.c. with virulent Y.pestis.

There was a 60% survival rate in Greer vaccinees against a challenge of 2×10$^5$ cfu Y.pestis (FIG. 1). By comparison, 80% of the combined microencapsulated F1+V (group 1) survived this challenge and there was 100% survival in group 2 (μV+pF1+10kg CTB). Thus the combined microencapsulated formulation was protective against virulent Y. pestis with no evidence of side effects.

In summary treatment groups were:

| Group | Treatment |
| --- | --- |
| 1. | 25 μg microencapsulated F1 (μ F1) + 25 μg microencapsulated V (μV) i.p. |
| 2. | 25 μg μ F1 + 25 μg μV + 10 μg CTB i.p. |
| 3. | 25 μg μ F1 i.p. |
| 4. | 25 μV i.p. |
| 5. | 25 μg F1 + 25 μg V in alhydrogel i.p. |
| 6. | Greer vaccine 0.1 ml i.m. |

Micro-encapsulation may also be carried out with block co-polymers, in the following experiments, model protein antigen BSA was used. The preparation and characterisation of microspheres is as follows. Protein-loaded microspheres were prepared by an oil/water solvent evaporation method procedure previously described see R. L. Hunter and B. Bennet. The J. Immunol., 133(6), 3167–3175 (1984), with some modifications. Polymer (poly-D-lactic acid): Resomer 206. Boehringer Ingelheim, Germany; 125 or 250 mg) solution in acetone (22.5 ml), containing model protein (antigen) BSA (at 15–25% theoretical loading level) and 0.11%w/v Pluronic L101 (or 0.09% w/v L121) available from Zeneca, probe sonicated for 10 seconds and then added to the aqueous phase (22.5 ml), mixing at 100 rpm for 5 minutes and rotary evaporated until the organic solvent had been removed. The resulting coiloid was washed and freeze-dried. Microspheres with an average diameter of ~1 μm (as determined by Malvern Mastersizer) and protein loadings ~0.5–1.0% produced in this fabrication condition. External morphology of the resulting microspheres were analysed by scanning electron microscopy (SEM). Surface characteristics were defined in terms of zeta potential and hydrophobicity.

Hydrophobicity measurements: hydrophobicity of microspheres was quantified using hydrophobic interaction chromatography (HIC) as previously reported see H. O. Alpar and A. J. Almeida, Eur. J. Pharm. Biopharm. 40, (4), 198–202 (1994). Microspheres were eluted from a series of agaroses which were modified with hydrophobic residues. The retention of microspheres in octyl agarose was used as an index of hydrophobicity.

Immunisation: A study was designed to establish the effects of differences in the type of microsphere and surface properties of the immune response. Female Balb/c mice (five per group) were injected i.m. with a single dose of BSA either encapsulated in Pluronic formulated microspheres or free in 100 μl alone or suspended in the presence of surfactant. The control group of mice received the same amount of antigen encapsulated into microspheres containing PVA as emulsion stabiliser. Tail tip blood samples were removed periodically for 2 months. The serum from each sample was analysed for anti-BSA antibody using an enzyme-linked immunosorbent assay (ELISA). Results are represented graphically in FIG. 2.

Figure 2:
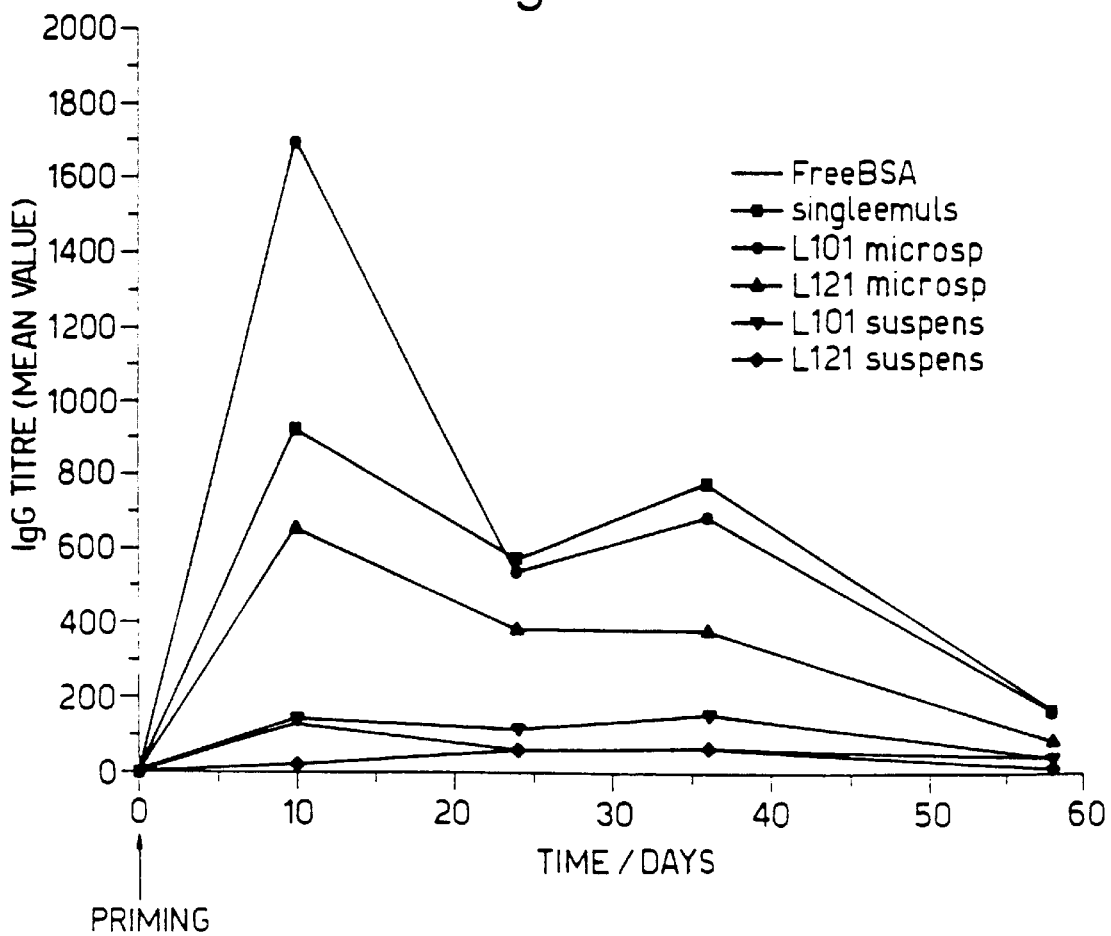
FIG. 2 illustrates in graphical form, IgG priming responses to intramuscular BSA immunisation in Balb/c mice.

The presence of Pluronic L101 and L121 endows the surface with a much higher degree of hydrophobicity compared to PVA formulations (70% retained on octyl agarose column as opposed to 30% latex control 95% retained). A hydrophobic surface would facilitate macrophage interactions and subsequent uptake and would therefore be much more likely to mediate increased immune response. FIG. 2 shows the effect of different BSA formulations in eliciting an immunoresponse. Batches formed by Pluronic L101 had a more enhanced effect on the plasma anti-BSA antibody titre than those formed by PVA. Batches formed by Pluronic L121 were slightly inferior to those of PVA microspheres in inducing good primary antibody response after delivery of only a small dose of antigen (1 μg). The higher serum IgG level obtained with Pluronic L101 preparations as compared to other preparations is noted and may partly be due to the higher surface hydrophobicity.

It was also mentioned earlier in the present application that DNA encoding the whole or part of the F1 antigen and DNA encoding the whole or part of the V antigen could be used directly, as a genetic vaccine. By way of example this may be carried out as follows.

1/ DNA encoding Y.pestis F1 and V is obtained by Polymerase Chain Reaction (PCR, amplification of specific regions of the *Y.pestis* genome, or by isolation of these genes from previously constructed plasmid clones e.g. for V exemplified sequence l.D. no 3.

2/ The F1 and V genes are cloned into mammalian expression vector plasmids such that the genes are situated downstream of a eukaryotic promoter. Suitable plasmids include pCMVβ (purchased from Clontech), in which the cytomegalovirus Immediate Early promoter is used. F1 and V may be cloned individually or in combination, and may be cloned as fusions with such genes as glutathione S-transferase, or eukaryotic signal sequences, which may stabilise the expressed protein and may facilitate export from mammalian cells.

3/ The recombinant plasmids are propagated in *Escherichia coli* and stocks are purified for transfection into a mammalian animal model and for immunisation of experimental animals by the intramuscular or intra-dermal or inhalational routes.

Example 1 To construct a DNA vaccine expressing V antigen, the plasmid vector pCMV was digested with restriction enzyme Not 1 to remove the lac Z gene coding sequence. The digested plasmid was treated with Klenow enzyme to create blunt-ended vector DNA. An ssp 1 restriction fragment containing the coding sequence for a fusion protein of V antigen and glutathione-S transferase was isolated from recombinant plasmid pVG100 and ligated to the vector DNA. The V sequence used in this case is that described in exemplified Seq. ID No. 3. The recombinant plasmid was transformed into *E coli* strain Nova Blue. Purifiea plasmid was inoculated into Balbic mice by intramuscular injection. Immunoglobulin responses to V antigen were detected in the serum of inoculated animals.

Example 2: To construct a DNA vaccine expressing F1 antigen, PCR primers were designed to amplify the complete caf1 open reading frame. This encodes F1 and its signal peptide which directs export of the protein from the bacterial cell. The PCR primers had "tails" at their 5' ends which contained restriction enzyme recognition sites to allow directional insertion into a plasmid vector. The sequences of the PCR primers, 5'FAB2 and 3'FBAM, are given in exemplified Seq.ID. No. 18 and Seq.ID No. 19, respectively.

5'FAB2 and 3'FBAM were used to amplify a PCR fragment, the sequence of which is given in exemplified Seq.ID.no. 20. The PCR fragment was digested with restriction enzymes Nhe 1 and Bam HI and cloned into the plasmid pBKCMV which had been digested with the same enzymes. The resulting plasmid, pF1AB was transformed into *E. coli* Nova Blue and purifies plasmid was used to inoculate Balb/c mice by intramuscular injection. Immunoglobulin responses to F1 were found in inoculated animals.

Example 3: To construct a DNA vaccine expressing both F1 and V, the coding sequence for V was inserted into the DNA vaccine expressing F1 . detailed in example 2. A linker region coding for 6 amino acids was positioned between the F1 and V coding sequences to allow each of the proteins to attain their conformational shape independantly. The linker-V coding sequence was obtained by digesting the recombinant plasmid placF /6 with Bam HI and Hind III. The linker-V DNA was ligated with the plasmid pFT$^{AB}$ which had also been digested with Bam HI and Hind III. The resulting plasmid. pFVAB. was transformed into cells of *E. coli* Nova Blue and stocks of plasmid were purified for further use. The nucleotide and derived amino acid sequence of the F1 /V fusion are given in exemplified Seq. ID No. 22.

An example of a fusion protein comprising both F1 and V antigens is described below.

Enzymes and reagents.

Materials for the preparation of growth media were obtained from Oxoid Ltd or Difco Laboratories. All enzymes used in the manipulation of DNA were obtained from Boehrinoer Mannheim UK Ltd and used according to the manufacturer's instructions. All other chemicals and biochemicals were obtained from Sigma Chemical Co unless otherwise indicated. Monospecific rabbit polyclonal anti-V serum was supplied by Dr R Brubaker (Department of Microbiology, Michigan State University) and mouse anti-F1 IgA monoclonal antibody (Mab) F13G8-1 was obtained from the American Type Culture Collection.

Bacterial strains and cultivation.

*Yersinia pestis* GS was cultured aerobically at 28° C. in a liquid medium (pH 6.8) containing 15 g proteose peptone, 2.5 g liver digest, 5 g yeast extract, 5 g NaCl per liter, supplemented with 80 ml of 0.25% haemin dissolved in 0.1M NaOH (Blood Base broth). *Eschedchia coli* JM109 was cultured and stored as described by Sambrook et al (Sambrook J et al. 1989. Molecular cloning, a laboratory manual. Cold Spring Harbor Laboratory Press, New York).

Manipulation of DNA.

Chromosomal DNA was isolated from *Y. pestis* by the method of Marmur (Marmur. J. 1961. J Mol Biol 3: 208–218). The genes encoding F1 antigen (caf1) and V antigen (IcrV) were amplified from *Y. pestis* DNA using PCR with 125 pmol of primers homologous to sequences from the 5' and 3' ends of the gene (Galyov, E E et al. 1990. FEBS Lett 277:230–232: Price S B et al. 1989. J Bacteriol 171: 5646–5653), although for caf1 only the region encoding the mature F1 antigen was amplified. The sequences of the primer (F/5'B: GATCGAGCTCGGCAGATTTAACTG-CAAG CACC), the F1 3' primer (Flink/3'A: GCATGGATCCTTGGTTAGATACGGT), the V 5' primer (Vlink/5'A: ATGGATCCATCGAAGGTCGTATTAGAGCCTACGAACAA), and the V 3' primer (VG/3'A. GCATAAGCTTCTAGTGTCATTTACCAGACGT) also included 5' tails encoding the restriction sites SacI BamHI, BamHI and HindIII, respectively. In addition the nucleotide A was altered from the published sequence of IcrV (Price S B et al. 1989. J Bacteriol 171: 5646–5653) to include an extra termination codon (TAA) in the amplified DNA. The tail of primer Vlink/5'A also included nucleotides encoding the factor Xa cleavage sequence lle-Glu-Gly-Arg. The PCR primers were prepared with a DNA synthesiser (model 392: Applied Biosystems). DNA fragments were obtained after 30 cycles of amplification (95° C., 20 s; 45° C., 20 s: 72° C., 30 s: model 9600 GeneAmp PCR System; Perkin Elmer) and the fragments were purified. The caf1 PCR product was digested with SacI and BamHI, ligated with suitably digested plasmid pUC18 and transformed into *E. coli* JM109 by electroporation. Subsequently, the IcrV-linker PCR product was digested with BamHI and HindIII, and ligated into the intermediate plasmid to form the recombinant plasmid placFV6. A colony containing placFV6 was identified by PCR using 30-mer primers (5' nucleotides located at positions 54 and 794 (Price S B et al. 1989. J Bacteriol 171: 5646–5653) which amplified an internal segment of the IcrV gene. To confirm the nucleotide sequence of the cloned insert, sequencing reactions containing placFV6 and primers designed from the caf1 and IcrV genes were performed using an automated Taq polymerase cycle sequencing protocol with fluorescently labelled dideoxy nucleotides (CATALYST Molecular Biology Labstation: Applied Biosystems). The reaction products were analysed using an automated DNA sequencer (model 373A: Applied Biosystems).

The DNA sequence and derived amino acid sequence of the cloned fusion protein is shown in Example 1. The fusion protein consists of F1 and V antigens separated by a six-amino acid linker Gly-Ser-lle-Glu-Gly-Arg. It is cloned downstream of the iac promoter and in-frame with the vector-encoded LacZ' fragment. Thus, the complete fusion protein encodes nine additional amino acids at the N-terminus (Met-Thr-Met-lle-Thr-Asn-er-Ser-Ser), and it accumulates in the cytoplasm.

Expression of the F1 /V fusion protein in *E. coli*.

Cultures of *E. coli* JM109/placFV6 were grown in LB containing 100 $\mu gml^{-1}$ ampicillin at 37° C. until the absorbance (600 nm) was 0.3. Isopropyl-D-thiogalactopyranoside (IPTG) was then added to the culture to a final concentration of 1 mM and growth was continued for a further 5 h. Whole cell lysates of the bacteria were prepared as described by Sambrook et al (Sambrook J et al. 1989. Molecular cloning, a laboratory manual. Cold Spring Harbor Laboratory Press, New York) and expression of the F1/V fusion protein was examined by SDS-PAGE on 10–15% gradient gels (Phastsystem, Pharmacia Biotech) and Western blotting (Sambrook J et al. 1989. Molecular cloning, a laboratory manual. Cold Spring Harbor Laboratory Press, N.Y.). Western blots were probed with rabbit anti-V serum at a dilution of 1/4000 or Mab F13G8-1 at a dilution of 1/250, and protein bands were visualised with a colloidal gold labelled secondary antibody (Auroprobe BLplus. Cambio) or an anti-mouse IgA secondary antibody conjugated to horse radish peroxidase (Sigma).

A fusion protein with an approximate molecular weight of 54.2 kDa was detected in lysates of JM109/placFV6 by Western blotting with anti-V and anti-F1 sera. This product was not detected in control lysates of JM109/pUC18.

Electroporation into Salmonella typhimurium SL3261.

Plasmid DNA was extracted and purified from JM109/placFV6 using a Qiaprep kit (Qiagen) and electroporated into S. typhimurium strain LB5010 (r- m+). Subsequently, modified placFP6 was isolated and electroporated in *S. typhimurium* strain SL3261 (aroA his). For inoculation into mice. bacteria were grown in LB containing 100 pgml$^{-1}$ ampicillin for 18 h without shaking. After washing, the cells were resuspended in 10% glycerol :n phosphate buffered saline (PBS) and stored at −70° C. The cell suspensions were defrosted and diluted in PBS as required prior to injection.

Immunisation with SL3261/placFVG.

Six week old female Balb/c mice. raised under specific pathogen-free conditions (Charles-River Laboratories, Margate, Kent, UK), were used in this study. A group of 19 mice received 0.1 ml immunising doses of approximately 5×10$^6$ cfu of SL3261/pFV6 on days 0 and 14 by the intravenous (iv) route. To retain placFV6 in vivo, mice were also injected subcutaneously (sc) with 50 $\mu$l ampicillin trihydrate suspension (150 mgml$^{-1}$; Penbritin injectable suspension POM: SmithKline Beecham Animal Health) for 5 days after each immunisation. In addition, groups of 15 mice were immunised iv on day 0 with a single 0.1 ml dose of approximately 5×10$^6$ cfu of SL3261 or intraperitoneally (ip) on days 0 and 14 with 0.1 ml of a mixture of 10 $\mu$g V and 10 $\mu$g F1 adsorbed to Alhydrogel. An untreated group of 10 age-matched mice were used as controls.

On day 7, five mice from the groups receiving SL3261/placFVe or SL3261 were sacrificed and their spleens were removed. The organs were homogenised in 5 ml of PES with a stomacher (Seward Medical Ltd) for 30 sec. The homogenates were serially diluted in PBS and inoculated on to L-agar or L-agar containing 100 $\mu gml^{-1}$ ampicillin to determine the number of bacteria per spleen.

| S. typhimurium | Actual dose | Average cfu per spleen ± sem[a] L-agar | L-amp | % recombinant |
|---|---|---|---|---|
| SL3261/placFV6 | 3.3 × 10$^6$ cfu | 1030 ± 294 | 380 ± 135 | 37% |
| SL3261 | 1.6 × 10$^7$ cfu | 1.85 × 10$^7$ ± 3.57 × 10$^6$ | | |

[a]standard error of the mean

Measurement of serum antibody titre.

On day 42, blood was sampled from the tail vein of mice immunised with SL32611placFV6 and pooled. The serum anti-V and anti-F1 titres were measured by a modified ELISA (Williamson, E D and R W Titball. 1993. Vaccine 11:1253–1258). Briefly, V (5 $\mu gml^{-1}$ in PBS) or F1 (2 ugml$^{-1}$) were coated on to a microtitre plate and the test sera were serially diluted in duplicate on the plate. Bound antibody was detected using peroxidase labelled conjugates of anti-mouse polyvalent Ig. The titre of specific antibody was estimated as the maximum dilution of serum giving an absorbance reading greater than 0.1 units, after subtraction of the absorbance due to non-specific binding detected in the control sera. The serum antibody titre was also determined for all groups of mice prior to challenge with *Y. pestis*.

On day 42, the anti-V and anti-F1 titres of mice receiving SL3261/placFV6 were 1:5120 and 1:2560, respectively.

Challenge with *Y. pestis*.

On day 57, groups of 5 or 7 mice from the immunised and control groups were challenged subcutaneously with 0.1 ml aliquots of *Y. pestis* strain GB containing 7.36×10$^2$ or 7.36×10$^4$ cfu. Strain GB was isolated from a fatal human case of plague and has a median lethal dose (MLD) of <1 cfu in Balbic mice by the s.c. route (Russell, P et al. 1995. Vaccine 13: 1551–1556). The mice were observed for 14 days and, where appropriate, the time to death was recorded. A post-mortem was carried out on all animals where possible. To test for the presence of *Y. pestis*, samples of blood, liver and spleen were smeared on to Congo Red agar and incubated at 28° C. for 48 h.

| Group | | Actual challenge dose – cfu | Survivors | MTD = sem[a] – hours |
|---|---|---|---|---|
| IV | SL3261/ | 7.36 × 10$^2$ | 6/7 | 320 |
| | placFV6 | 7.36 × 10$^4$ | 6/7 | 124 |
| | SL3261 | 7.36 × 10$^2$ | 0/5 | 97.4 ± 17.8 |
| | | 7.36 × 10$^4$ | 0/5 | 97.6 ± 18.9 |
| IP | F1 – V | 7.36 × 10$^2$ | 7/7 | — |
| | | 7.36 × 10$^4$ | 6/7 | 184 |
| | Controls | 7.36 × 10$^2$ | 0/5 | 116.8 ± 4.8 |
| | | 7.36 × 10$^4$ | 0/5 | 63.6 ± 6.9 |

[a]standard error of the mean

We claim:

1. A method of protecting a human or animal body from the effects of infection with *Yersinia pestis* comprising administering to the body a vaccine consisting essentially of isolated or purified *Yersinia pestis* V antigen and *Yersinia pestis* F1 antigen or a protective epitopic part of each of these in a form other than whole *Yersinia pestis* organisms.

2. A method as claimed in claim 1 wherein the antigens are administered in the form of a live vaccine.

3. A method as claimed in claim 2 wherein the live vaccine comprises human or animal gut colonising organisms that have been transformed using recombinant DNA to enable each organism to express both of V antigen and F1 antigen.

4. A method as claimed in claim 3 wherein the gut colonising organisms have been transformed with recombinant DNA such that they are enabled to express a fusion protein comprising both V and F1 antigen amino acid sequences or a protective epitopic part of each.

5. A method as claimed in claim 3 wherein the DNA comprises DNA of SEQ ID No 1 orSEQ ID No 3.

6. A method as claimed in claim 5 wherein the DNA is positioned in frame with a promoter selected from be group consisting of the Iacz promoter or Nirβ promoter.

7. A method as claimed in claim 3 wherein the DNA comprises DNA of SEQ ID No 10.

8. A method as claimed in claim 1 wherein the antigens are provided in a pharmaceutically acceptable carrier.

9. A method as claimed in claim 8 wherein the carrier is such as to proouce an oil-in-water emulsion.

10. A method as claimed in claim 1 wherein the vaccine includes an adjuvant.

11. A method as claimed in claim 1 wherein the vaccine is administered such that it is enabled to induce local stimulation of the gut-associated lymphoid tissue (GALT) and, by trafficking of lymphocytes through the common mucosal immune system provide a secondary stimulation of the bronchial associated lymphoid tissue (BALT) such that a secretory IgA response is achieved at the respiratory mucosal surface.

12. A method as claimed in claim 1 wherein the vaccine is in the form of droplets or capsules.

13. A method as claimed in claim 12 wherein the capsules are liposomes or microcapsules effective in delivering the composition to the airways of an individual for the purposes of evoking mucosal immune response.

14. A vaccine consisting essentially of isolated or purified recombinant Yersinia pestis V antigen and Yersiniapestis F1 antigen or a protective epitopic part of each of these in a form other than whole *Yersinia pestis* organisms.

15. A vaccine as claimed in claim 14 characterised in that it is a live vaccine.

16. vaccine as claimed in claim 15 wherein the live vaccine comprises human or animal gut colonising organisms that have been transformed using recombinant DNA to enable them to express one or both of V antigen and F1 antigen.

17. A vaccine as claimed in claim 16 wherein the gut colonising organisms have been transformed with recombinant DNA such that they are enabled to express a fusion protein comprising both V and F1 antigen amino acid sequences or a protective epitopic part of each.

18. A vaccine as claimed in claim 16 wherein the DNA comprises DNA of SEQ ID No 1 or SEQ ID No 3.

19. A vaccine as claimed in claim 18 wherein the DNA is positioned in frame with a lacz or nirβ promoter.

20. A vaccine as claimed in claim 16 wherein the DNA comprises DNA of SEQ ID No 10.

21. A vaccine as claimed in claim 14 wherein the antigens are provided in a pharmaceutically acceptable carrier.

22. A vaccine as claimed in claim 21 wherein the carrier is such as to produce an oil-in-water emulsion.

23. A vaccine as claimed in claim 14 or 21 characterised in that it includes an adjuvant.

24. A vaccine as claimed in claim 14 or 21 characterised in that it is in the form of droplets or capsules.

25. A vaccine as claimed in claim 24 wherein the capsules are liposomes or microcapsules effective in delivering the composition to the airways of an individual for the purposes of evoking mucosal immune response.

26. A vaccine as claimed in claim 24 wherein the capsules are block co-polymers.

27. A vaccine as claimed in claim 24 wherein the capsules comprise biodegradable polymers.

28. A vaccine as claimed in claim 27 wherein the biodegradable polymer is poly-lactic acid.

29. A vaccine as claimed in claim 28 further comprising glycollic acid.

30. A vaccine as claimed in claim 28 further comprising block co-polymer.

31. A vaccine according to either of claims 26 in which the block co-polymer contains the repeat unit $(POP-POE)_n$.

32. A method as claimed in claim 5 wherein the DNA is positioned in frame with an in-vivo inducible promoter.

33. A method according to claim 32 wherein the in-vivo inducible promoter is selected from HtrA, nirβ, OmpR, OmpC, or PhoP.

34. A method as claimed in claim 5 wherein the DNA is positioned in frame with a constitutive promoter.

35. A method according to claim 34 wherein the constitutive promoter is Osmz or lacz.

36. A method as claimed in claim 3 wherein the DNA comprises DNA of SEQ ID No 7 or 8 or 9.

37. A method as claimed in claim 3 wherein the DNA comprises DNA of SEQ ID No 16.

38. A method as claimed in either of claim 3 wherein the vaccine comprises DNA of any one of the following SEQ ID Nos: 1, 3 and 10.

39. A method as claimed in claim 4 wherein the DNA comprises DNA of SEQ ID No 20 or 22.

40. A method as claimed in claim 39 wherein the DNA is positioned down-stream of a eukaryotic promoter.

41. A method according to claim 40 wherein the eukaryotic promoter is a CMV immediate early promoter.

42. A method as claimed in claim 8 wherein the carrier is water.

43. A vaccine as claimed in claim 16 wherein the DNA comprises DNA of any of the sequences 7,8,9,10, and 16.

44. A vaccine as claimed in claim 18 wherein the DNA is positioned in frame with an in-vivo inducible promoter selected from the group consisting of htrA, nirB, ompR, ompC and phoP.

45. A vaccine as claimed in claim 18 wherein the DNA is positioned in frame with a constitutive promoter selected from Osmz or lacz.

46. A vaccine as claimed in claim 18 wherein the DNA is positioned downstream of a eukaryotic promoter.

47. A vaccine as claimed in claim 46 wherein the DNA comprises DNA of SEQ ID No 20 or 22.

48. A vaccine according to claim 21 wherein the carrier is water.

* * * * *

SEQUENCE LISTING (1) GENERAL INFORMATION:

(iii) NUMBER OF SEQUENCES: 24

(2) INFORMATION FOR SEQ ID NO:1:

(i) SEQUENCE CHARACTERISTICS:
       (A) LENGTH: 1014 base pairs
       (B) TYPE: nucleic acid
       (C) STRANDEDNESS: double
       (D) TOPOLOGY: linear (ii) MOLECULE TYPE: cDNA (iii) HYPOTHETICAL: NO (iv) ANTI-SENSE: NO (vi) ORIGINAL SOURCE:
       (A) ORGANISM: Yersinia pestis (ix) FEATURE:
       (A) NAME/KEY: CDS
       (B) LOCATION: 1..987

(xi) SEQUENCE DESCRIPTION: SEQ ID NO:1:

```
ATT TCA GAA TTC ATT AGA GCC TAC GAA CAA AAC CCA CAA CAT TTT ATT      48
Ile Ser Glu Phe Ile Arg Ala Tyr Glu Gln Asn Pro Gln His Phe Ile
 1               5                  10                  15

GAG GAT CTA GAA AAA GTT AGG GTG GAA CAA CTT ACT GGT CAT GGT TCT      96
Glu Asp Leu Glu Lys Val Arg Val Glu Gln Leu Thr Gly His Gly Ser
             20                  25                  30

TCA GTT TTA GAA GAA TTG GTT CAG TTA GTC AAA GAT AAA AAT ATA GAT     144
Ser Val Leu Glu Glu Leu Val Gln Leu Val Lys Asp Lys Asn Ile Asp
         35                  40                  45

ATT TCC ATT AAA TAT GAT CCC AGA AAA GAT TCG GAG GTT TTT GCC AAT     192
Ile Ser Ile Lys Tyr Asp Pro Arg Lys Asp Ser Glu Val Phe Ala Asn
     50                  55                  60

AGA GTA ATT ACT GAT GAT ATC GAA TTG CTC AAG AAA ATC CTA GCT TAT     240
Arg Val Ile Thr Asp Asp Ile Glu Leu Leu Lys Lys Ile Leu Ala Tyr
 65                  70                  75                  80

TTT CTA CCC GAG GAT GCC ATT CTT AAA GGC GGT CAT TAT GAC AAC CAA     288
Phe Leu Pro Glu Asp Ala Ile Leu Lys Gly Gly His Tyr Asp Asn Gln
                 85                  90                  95

CTG CAA AAT GGC ATC AAG CGA GTA AAA GAG TTC CTT GAA TCA TCG CCG     336
Leu Gln Asn Gly Ile Lys Arg Val Lys Glu Phe Leu Glu Ser Ser Pro
            100                 105                 110

AAT ACA CAA TGG GAA TTG CGG GCG TTC ATG GCA GTA ATG CAT TTC TCT     384
Asn Thr Gln Trp Glu Leu Arg Ala Phe Met Ala Val Met His Phe Ser
        115                 120                 125

TTA ACC GCC GAT CGT ATC GAT GAT GAT ATT TTG AAA GTG ATT GTT GAT     432
Leu Thr Ala Asp Arg Ile Asp Asp Asp Ile Leu Lys Val Ile Val Asp
    130                 135                 140

TCA ATG AAT CAT CAT GGT GAT GCC CGT AGC AAG TTG CGT GAA GAA TTA     480
Ser Met Asn His His Gly Asp Ala Arg Ser Lys Leu Arg Glu Glu Leu
145                 150                 155                 160

GCT GAG CTT ACC GCC GAA TTA AAG ATT TAT TCA GTT ATT CAA GCC GAA     528
Ala Glu Leu Thr Ala Glu Leu Lys Ile Tyr Ser Val Ile Gln Ala Glu
                165                 170                 175

ATT AAT AAG CAT CTG TCT AGT AGT GGC ACC ATA AAT ATC CAT GAT AAA     576
Ile Asn Lys His Leu Ser Ser Ser Gly Thr Ile Asn Ile His Asp Lys
            180                 185                 190

TCC ATT AAT CTC ATG GAT AAA AAT TTA TAT GGT TAT ACA GAT GAA GAG     624
```

```
Ser Ile Asn Leu Met Asp Lys Asn Leu Tyr Gly Tyr Thr Asp Glu Glu
            195                 200                 205

ATT TTT AAA GCC AGC GCA GAG TAC AAA ATT CTC GAG AAA ATG CCT CAA        672
Ile Phe Lys Ala Ser Ala Glu Tyr Lys Ile Leu Glu Lys Met Pro Gln
    210                 215                 220

ACC ACC ATT CAG GTG GAT GGG AGC GAG AAA AAA ATA GTC TCG ATA AAG        720
Thr Thr Ile Gln Val Asp Gly Ser Glu Lys Lys Ile Val Ser Ile Lys
225                 230                 235                 240

GAC TTT CTT GGA AGT GAG AAT AAA AGA ACC GGG GCG TTG GGT AAT CTG        768
Asp Phe Leu Gly Ser Glu Asn Lys Arg Thr Gly Ala Leu Gly Asn Leu
                245                 250                 255

AAA AAC TCA TAC TCT TAT AAT AAA GAT AAT AAT GAA TTA TCT CAC TTT        816
Lys Asn Ser Tyr Ser Tyr Asn Lys Asp Asn Asn Glu Leu Ser His Phe
            260                 265                 270

GCC ACC ACC TGC TCG GAT AAG TCC AGG CCG CTC AAC GAC TTG GTT AGC        864
Ala Thr Thr Cys Ser Asp Lys Ser Arg Pro Leu Asn Asp Leu Val Ser
        275                 280                 285

CAA AAA ACA ACT CAG CTG TCT GAT ATT ACA TCA CGT TTT AAT TCA GCT        912
Gln Lys Thr Thr Gln Leu Ser Asp Ile Thr Ser Arg Phe Asn Ser Ala
290                 295                 300

ATT GAA GCA CTG AAC CGT TTC ATT CAG AAA TAT GAT TCA GTG ATG CAA        960
Ile Glu Ala Leu Asn Arg Phe Ile Gln Lys Tyr Asp Ser Val Met Gln
305                 310                 315                 320

CGT CTG CTA GAT GAC ACG TCT GGT AAA TGACACGAGG TAATTATGTA             1007
Arg Leu Leu Asp Asp Thr Ser Gly Lys
                325

AGTCGAC                                                                1014

(2) INFORMATION FOR SEQ ID NO:2:

(i) SEQUENCE CHARACTERISTICS:
        (A) LENGTH: 329 amino acids
        (B) TYPE: amino acid
        (D) TOPOLOGY: linear (ii) MOLECULE TYPE: protein (xi) SEQUENCE DESCRIPTION: SEQ ID NO:2:

Ile Ser Glu Phe Ile Arg Ala Tyr Glu Gln Asn Pro Gln His Phe Ile
1               5                   10                  15

Glu Asp Leu Glu Lys Val Arg Val Glu Gln Leu Thr Gly His Gly Ser
            20                  25                  30

Ser Val Leu Glu Glu Leu Val Gln Leu Val Lys Asp Lys Asn Ile Asp
        35                  40                  45

Ile Ser Ile Lys Tyr Asp Pro Arg Lys Asp Ser Glu Val Phe Ala Asn
    50                  55                  60

Arg Val Ile Thr Asp Asp Ile Glu Leu Leu Lys Lys Ile Leu Ala Tyr
65                  70                  75                  80

Phe Leu Pro Glu Asp Ala Ile Leu Lys Gly Gly His Tyr Asp Asn Gln
                85                  90                  95

Leu Gln Asn Gly Ile Lys Arg Val Lys Glu Phe Leu Glu Ser Ser Pro
            100                 105                 110

Asn Thr Gln Trp Glu Leu Arg Ala Phe Met Ala Val Met His Phe Ser
        115                 120                 125

Leu Thr Ala Asp Arg Ile Asp Asp Ile Leu Lys Val Ile Val Asp
    130                 135                 140

Ser Met Asn His His Gly Asp Ala Arg Ser Lys Leu Arg Glu Glu Leu
145                 150                 155                 160

Ala Glu Leu Thr Ala Glu Leu Lys Ile Tyr Ser Val Ile Gln Ala Glu
```

```
                        165                 170                 175
Ile Asn Lys His Leu Ser Ser Gly Thr Ile Asn Ile His Asp Lys
            180                 185                 190
Ser Ile Asn Leu Met Asp Lys Asn Leu Tyr Gly Tyr Thr Asp Glu Glu
        195                 200                 205
Ile Phe Lys Ala Ser Ala Glu Tyr Lys Ile Leu Glu Lys Met Pro Gln
    210                 215                 220
Thr Thr Ile Gln Val Asp Gly Ser Glu Lys Lys Ile Val Ser Ile Lys
225                 230                 235                 240
Asp Phe Leu Gly Ser Glu Asn Lys Arg Thr Gly Ala Leu Gly Asn Leu
                245                 250                 255
Lys Asn Ser Tyr Ser Tyr Asn Lys Asp Asn Asn Glu Leu Ser His Phe
            260                 265                 270
Ala Thr Thr Cys Ser Asp Lys Ser Arg Pro Leu Asn Asp Leu Val Ser
        275                 280                 285
Gln Lys Thr Thr Gln Leu Ser Asp Ile Thr Ser Arg Phe Asn Ser Ala
    290                 295                 300
Ile Glu Ala Leu Asn Arg Phe Ile Gln Lys Tyr Asp Ser Val Met Gln
305                 310                 315                 320
Arg Leu Leu Asp Asp Thr Ser Gly Lys
                325

(2) INFORMATION FOR SEQ ID NO:3:

(i) SEQUENCE CHARACTERISTICS:
        (A) LENGTH: 1014 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Yersinia pestis (ix) FEATURE:
        (A) NAME/KEY: CDS
        (B) LOCATION: 1..987

(xi) SEQUENCE DESCRIPTION: SEQ ID NO:3:

GGG ATC CCC GGA ATT CGA GCC TAC GAA CAA AAC CCA CAA CAT TTT ATT       48
Gly Ile Pro Gly Ile Arg Ala Tyr Glu Gln Asn Pro Gln His Phe Ile
 1               5                  10                  15

GAG GAT CTA GAA AAA GTT AGG GTG GAA CAA CTT ACT GGT CAT GGT TCT       96
Glu Asp Leu Glu Lys Val Arg Val Glu Gln Leu Thr Gly His Gly Ser
            20                  25                  30

TCA GTT TTA GAA GAA TTG GTT CAG TTA GTC AAA GAT AAA AAT ATA GAT      144
Ser Val Leu Glu Glu Leu Val Gln Leu Val Lys Asp Lys Asn Ile Asp
        35                  40                  45

ATT TCC ATT AAA TAT GAT CCC AGA AAA GAT TCG GAG GTT TTT GCC AAT      192
Ile Ser Ile Lys Tyr Asp Pro Arg Lys Asp Ser Glu Val Phe Ala Asn
    50                  55                  60

AGA GTA ATT ACT GAT GAT ATC GAA TTG CTC AAG AAA ATC CTA GCT TAT      240
Arg Val Ile Thr Asp Asp Ile Glu Leu Leu Lys Lys Ile Leu Ala Tyr
65                  70                  75                  80

TTT CTA CCC GAG GAT GCC ATT CTT AAA GGC GGT CAT TAT GAC AAC CAA      288
Phe Leu Pro Glu Asp Ala Ile Leu Lys Gly Gly His Tyr Asp Asn Gln
                85                  90                  95
```

```
CTG CAA AAT GGC ATC AAG CGA GTA AAA GAG TTC CTT GAA TCA TCG CCG    336
Leu Gln Asn Gly Ile Lys Arg Val Lys Glu Phe Leu Glu Ser Ser Pro
        100                 105                 110

AAT ACA CAA TGG GAA TTG CGG GCG TTC ATG GCA GTA ATG CAT TTC TCT    384
Asn Thr Gln Trp Glu Leu Arg Ala Phe Met Ala Val Met His Phe Ser
        115                 120                 125

TTA ACC GCC GAT CGT ATC GAT GAT GAT ATT TTG AAA GTG ATT GTT GAT    432
Leu Thr Ala Asp Arg Ile Asp Asp Asp Ile Leu Lys Val Ile Val Asp
130                 135                 140

TCA ATG AAT CAT CAT GGT GAT GCC CGT AGC AAG TTG CGT GAA GAA TTA    480
Ser Met Asn His His Gly Asp Ala Arg Ser Lys Leu Arg Glu Glu Leu
145                 150                 155                 160

GCT GAG CTT ACC GCC GAA TTA AAG ATT TAT TCA GTT ATT CAA GCC GAA    528
Ala Glu Leu Thr Ala Glu Leu Lys Ile Tyr Ser Val Ile Gln Ala Glu
                165                 170                 175

ATT AAT AAG CAT CTG TCT AGT AGT GGC ACC ATA AAT ATC CAT GAT AAA    576
Ile Asn Lys His Leu Ser Ser Ser Gly Thr Ile Asn Ile His Asp Lys
                180                 185                 190

TCC ATT AAT CTC ATG GAT AAA AAT TTA TAT GGT TAT ACA GAT GAA GAG    624
Ser Ile Asn Leu Met Asp Lys Asn Leu Tyr Gly Tyr Thr Asp Glu Glu
                195                 200                 205

ATT TTT AAA GCC AGC GCA GAG TAC AAA ATT CTC GAG AAA ATG CCT CAA    672
Ile Phe Lys Ala Ser Ala Glu Tyr Lys Ile Leu Glu Lys Met Pro Gln
210                 215                 220

ACC ACC ATT CAG GTG GAT GGG AGC GAG AAA AAA ATA GTC TCG ATA AAG    720
Thr Thr Ile Gln Val Asp Gly Ser Glu Lys Lys Ile Val Ser Ile Lys
225                 230                 235                 240

GAC TTT CTT GGA AGT GAG AAT AAA AGA ACC GGG GCG TTG GGT AAT CTG    768
Asp Phe Leu Gly Ser Glu Asn Lys Arg Thr Gly Ala Leu Gly Asn Leu
                245                 250                 255

AAA AAC TCA TAC TCT TAT AAT AAA GAT AAT AAT GAA TTA TCT CAC TTT    816
Lys Asn Ser Tyr Ser Tyr Asn Lys Asp Asn Asn Glu Leu Ser His Phe
                260                 265                 270

GCC ACC ACC TGC TCG GAT AAG TCC AGG CCG CTC AAC GAC TTG GTT AGC    864
Ala Thr Thr Cys Ser Asp Lys Ser Arg Pro Leu Asn Asp Leu Val Ser
                275                 280                 285

CAA AAA ACA ACT CAG CTG TCT GAT ATT ACA TCA CGT TTT AAT TCA GCT    912
Gln Lys Thr Thr Gln Leu Ser Asp Ile Thr Ser Arg Phe Asn Ser Ala
290                 295                 300

ATT GAA GCA CTG AAC CGT TTC ATT CAG AAA TAT GAT TCA GTG ATG CAA    960
Ile Glu Ala Leu Asn Arg Phe Ile Gln Lys Tyr Asp Ser Val Met Gln
305                 310                 315                 320

CGT CTG CTA GAT GAC ACG TCT GGT AAA TGACACGAGG TAATTATGTA         1007
Arg Leu Leu Asp Asp Thr Ser Gly Lys
                325

AGTCGAC                                                           1014
```

(2) INFORMATION FOR SEQ ID NO:4:

(i) SEQUENCE CHARACTERISTICS:
        (A) LENGTH: 329 amino acids
        (B) TYPE: amino acid
        (D) TOPOLOGY: linear (ii) MOLECULE TYPE: protein (xi) SEQUENCE DESCRIPTION: SEQ ID NO:4:

```
Gly Ile Pro Gly Ile Arg Ala Tyr Glu Gln Asn Pro Gln His Phe Ile
 1               5                  10                  15

Glu Asp Leu Glu Lys Val Arg Val Glu Gln Leu Thr Gly His Gly Ser
            20                  25                  30
```

Ser Val Leu Glu Glu Leu Val Gln Leu Val Lys Asp Lys Asn Ile Asp
            35                  40                  45

Ile Ser Ile Lys Tyr Asp Pro Arg Lys Asp Ser Glu Val Phe Ala Asn
 50                  55                  60

Arg Val Ile Thr Asp Asp Ile Glu Leu Leu Lys Lys Ile Leu Ala Tyr
 65                  70                  75                  80

Phe Leu Pro Glu Asp Ala Ile Leu Lys Gly Gly His Tyr Asp Asn Gln
                85                  90                  95

Leu Gln Asn Gly Ile Lys Arg Val Lys Glu Phe Leu Glu Ser Ser Pro
            100                 105                 110

Asn Thr Gln Trp Glu Leu Arg Ala Phe Met Ala Val Met His Phe Ser
            115                 120                 125

Leu Thr Ala Asp Arg Ile Asp Asp Ile Leu Lys Val Ile Val Asp
 130                 135                 140

Ser Met Asn His His Gly Asp Ala Arg Ser Lys Leu Arg Glu Glu Leu
 145                 150                 155                 160

Ala Glu Leu Thr Ala Glu Leu Lys Ile Tyr Ser Val Ile Gln Ala Glu
                165                 170                 175

Ile Asn Lys His Leu Ser Ser Gly Thr Ile Asn Ile His Asp Lys
                180                 185                 190

Ser Ile Asn Leu Met Asp Lys Asn Leu Tyr Gly Tyr Thr Asp Glu Glu
 195                 200                 205

Ile Phe Lys Ala Ser Ala Glu Tyr Lys Ile Leu Glu Lys Met Pro Gln
 210                 215                 220

Thr Thr Ile Gln Val Asp Gly Ser Glu Lys Lys Ile Val Ser Ile Lys
 225                 230                 235                 240

Asp Phe Leu Gly Ser Glu Asn Lys Arg Thr Gly Ala Leu Gly Asn Leu
                245                 250                 255

Lys Asn Ser Tyr Ser Tyr Asn Lys Asp Asn Asn Glu Leu Ser His Phe
                260                 265                 270

Ala Thr Thr Cys Ser Asp Lys Ser Arg Pro Leu Asn Asp Leu Val Ser
                275                 280                 285

Gln Lys Thr Thr Gln Leu Ser Asp Ile Thr Ser Arg Phe Asn Ser Ala
            290                 295                 300

Ile Glu Ala Leu Asn Arg Phe Ile Gln Lys Tyr Asp Ser Val Met Gln
305                 310                 315                 320

Arg Leu Leu Asp Asp Thr Ser Gly Lys
                325

(2) INFORMATION FOR SEQ ID NO:5:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Yersinia pestis (xi) SEQUENCE DESCRIPTION: SEQ ID NO:5:

GATCGAATTC GAGCCTACGA ACAA                                           24

(2) INFORMATION FOR SEQ ID NO:6:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Yersinia pestis (xi) SEQUENCE DESCRIPTION: SEQ ID NO:6:

GGATCGTCGA CTTACATAAT TACCTCGTGT CA                         32

(2) INFORMATION FOR SEQ ID NO:7:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Yersinia pestis (xi) SEQUENCE DESCRIPTION: SEQ ID NO:7:

GATCGAGCTC GGCAGATTTA ACTGCAAGCA CC                         32

(2) INFORMATION FOR SEQ ID NO:8:

(i) SEQUENCE CHARACTERISTICS:
        (A) LENGTH: 35 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Yersinia pestis (xi) SEQUENCE DESCRIPTION: SEQ ID NO:8:

CAGGTCGAGC TCGTCGACGG TTAGGCTCAA AGTAG                      35

(2) INFORMATION FOR SEQ ID NO:9:

(i) SEQUENCE CHARACTERISTICS:
        (A) LENGTH: 25 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
    (A) ORGANISM: Yersinia pestis (xi) SEQUENCE DESCRIPTION: SEQ ID NO:9:

```
TGGTACGCTT ACTCTTGGCG GCTAT                                        25
```

(2) INFORMATION FOR SEQ ID NO:10:

(i) SEQUENCE CHARACTERISTICS:
      (A) LENGTH: 541 base pairs
      (B) TYPE: nucleic acid
      (C) STRANDEDNESS: double
      (D) TOPOLOGY: linear (ii) MOLECULE TYPE: cDNA (iii) HYPOTHETICAL: NO (iv) ANTI-SENSE: NO (vi) ORIGINAL SOURCE:
      (A) ORGANISM: Yersinia pestis (ix) FEATURE:
      (A) NAME/KEY: CDS
      (B) LOCATION: 2..454

(ix) FEATURE:
      (A) NAME/KEY: misc_recomb
      (B) LOCATION: 1..6

(ix) FEATURE:
      (A) NAME/KEY: misc_recomb
      (B) LOCATION: 536..541

(xi) SEQUENCE DESCRIPTION: SEQ ID NO:10:

```
G AGC TCG GCA GAT TTA ACT GCA AGC ACC ACT GCA ACG GCA ACT CTT        46
  Ser Ser Ala Asp Leu Thr Ala Ser Thr Thr Ala Thr Ala Thr Leu
   1               5                  10                  15

GTT GAA CCA GCC CGC ATC ACT ATT ACA TAT AAG GAA GGC GCT CCA ATT      94
Val Glu Pro Ala Arg Ile Thr Ile Thr Tyr Lys Glu Gly Ala Pro Ile
                 20                  25                  30

ACA ATT ATG GAC AAT GGA AAC ATC GAT ACA GAA TTA CTT GTT GGT ACG     142
Thr Ile Met Asp Asn Gly Asn Ile Asp Thr Glu Leu Leu Val Gly Thr
             35                  40                  45

CTT ACT CTT GGC GGC TAT AAA ACA GGA ACC ACT AGC ACA TCT GTT AAC     190
Leu Thr Leu Gly Gly Tyr Lys Thr Gly Thr Thr Ser Thr Ser Val Asn
         50                  55                  60

TTT ACA GAT GCC GCG GGT GAT CCC ATG TAC TTA ACA TTT ACT TCT CAG     238
Phe Thr Asp Ala Ala Gly Asp Pro Met Tyr Leu Thr Phe Thr Ser Gln
     65                  70                  75

GAT GGA AAT AAC CAC CAA TTC ACT ACA AAA GTG ATT GGC AAG GAT TCT     286
Asp Gly Asn Asn His Gln Phe Thr Thr Lys Val Ile Gly Lys Asp Ser
 80                  85                  90                  95

AGA GAT TTT GAT ATC TCT CCT AAG GTA AAC GGT GAG AAC CTT GTG GGG     334
Arg Asp Phe Asp Ile Ser Pro Lys Val Asn Gly Glu Asn Leu Val Gly
                100                 105                 110

GAT GAC GTC GTC TTG GCT ACG GGC AGC CAG GAT TTC TTT GTT CGC TCA     382
Asp Asp Val Val Leu Ala Thr Gly Ser Gln Asp Phe Phe Val Arg Ser
            115                 120                 125

ATT GGT TCC AAA GGC GGT AAA CTT GCA GCA GGT AAA TAC ACT GAT GCT     430
Ile Gly Ser Lys Gly Gly Lys Leu Ala Ala Gly Lys Tyr Thr Asp Ala
        130                 135                 140

GTA ACC GTA ACC GTA TCT AAC CAA TAATCCATAT AGATAATAGA TAAAGGAGGG    484
Val Thr Val Thr Val Ser Asn Gln
    145                 150

CTATTATGCC CTCCTTTAAT ATTTATGAAT TATCCTACTT TGAGCCTAAC CGTCGAC      541
```

(2) INFORMATION FOR SEQ ID NO:11:

(i) SEQUENCE CHARACTERISTICS:
        (A) LENGTH: 151 amino acids
        (B) TYPE: amino acid
        (D) TOPOLOGY: linear (ii) MOLECULE TYPE: protein (xi) SEQUENCE DESCRIPTION: SEQ ID NO:11:

```
Ser Ser Ala Asp Leu Thr Ala Ser Thr Thr Ala Thr Ala Thr Leu Val
 1               5                  10                  15

Glu Pro Ala Arg Ile Thr Ile Thr Tyr Lys Glu Gly Ala Pro Ile Thr
                20                  25                  30

Ile Met Asp Asn Gly Asn Ile Asp Thr Glu Leu Leu Val Gly Thr Leu
            35                  40                  45

Thr Leu Gly Gly Tyr Lys Thr Gly Thr Thr Ser Thr Ser Val Asn Phe
    50                  55                  60

Thr Asp Ala Ala Gly Asp Pro Met Tyr Leu Thr Phe Thr Ser Gln Asp
65                  70                  75                  80

Gly Asn Asn His Gln Phe Thr Thr Lys Val Ile Gly Lys Asp Ser Arg
                85                  90                  95

Asp Phe Asp Ile Ser Pro Lys Val Asn Gly Glu Asn Leu Val Gly Asp
               100                 105                 110

Asp Val Val Leu Ala Thr Gly Ser Gln Asp Phe Phe Val Arg Ser Ile
           115                 120                 125

Gly Ser Lys Gly Gly Lys Leu Ala Ala Gly Lys Tyr Thr Asp Ala Val
       130                 135                 140

Thr Val Thr Val Ser Asn Gln
145                 150
```

(2) INFORMATION FOR SEQ ID NO:12:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Yersinia pestis (xi) SEQUENCE DESCRIPTION: SEQ ID NO:12:

TCGCCCGGGA ATTCCGAACA TAAATCGGTT CAGTGGCC                     38

(2) INFORMATION FOR SEQ ID NO:13:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO

```
        (vi) ORIGINAL SOURCE:
             (A) ORGANISM: Yersinia pestis (xi) SEQUENCE DESCRIPTION: SEQ ID NO:13:

GGCGTATTCC TCGCTAGCAA TGTTTAACG                                      29

(2) INFORMATION FOR SEQ ID NO:14:

(i) SEQUENCE CHARACTERISTICS:
             (A) LENGTH: 31 base pairs
             (B) TYPE: nucleic acid
             (C) STRANDEDNESS: single
             (D) TOPOLOGY: linear (ii) MOLECULE TYPE: DNA (genomic)

(iii) HYPOTHETICAL: NO (iv) ANTI-SENSE: NO (vi) ORIGINAL SOURCE:
             (A) ORGANISM: Yersinia pestis (xi) SEQUENCE DESCRIPTION: SEQ ID NO:14:

ATCGTTAAAC ATTGCTAGCG AGGAATACGC C                                   31

(2) INFORMATION FOR SEQ ID NO:15:

(i) SEQUENCE CHARACTERISTICS:
             (A) LENGTH: 39 base pairs
             (B) TYPE: nucleic acid
             (C) STRANDEDNESS: single
             (D) TOPOLOGY: linear (ii) MOLECULE TYPE: DNA (genomic)

(iii) HYPOTHETICAL: NO (iv) ANTI-SENSE: NO (vi) ORIGINAL SOURCE:
             (A) ORGANISM: Yersinia pestis (xi) SEQUENCE DESCRIPTION: SEQ ID NO:15:

GATAGATCTG TCGACTGAAC CTATTATATT GCTTCGCGC                           39

(2) INFORMATION FOR SEQ ID NO:16:

(i) SEQUENCE CHARACTERISTICS:
             (A) LENGTH: 1462 base pairs
             (B) TYPE: nucleic acid
             (C) STRANDEDNESS: double
             (D) TOPOLOGY: linear (ii) MOLECULE TYPE: cDNA (iii) HYPOTHETICAL: NO (iv) ANTI-SENSE: NO (vi) ORIGINAL SOURCE:
             (A) ORGANISM: Yersinia pestis (ix) FEATURE:
             (A) NAME/KEY: CDS
             (B) LOCATION: 8..1447

(xi) SEQUENCE DESCRIPTION: SEQ ID NO:16:

GAGCTCG GCA GAT TTA ACT GCA AGC ACC ACT GCA ACG GCA ACT CTT GTT      49
        Ala Asp Leu Thr Ala Ser Thr Thr Ala Thr Ala Thr Leu Val
         1               5                  10

GAA CCA GCC CGC ATC ACT CTT ACA TAT AAG GAA GGC GCT CCA ATT ACA      97
```

|   |   |   |   |   |   |   |   |   |   |   |   |   |   |   |   |   |
|---|---|---|---|---|---|---|---|---|---|---|---|---|---|---|---|---|
| Glu | Pro | Ala | Arg | Ile | Thr | Leu | Thr | Tyr | Lys | Glu | Gly | Ala | Pro | Ile | Thr | |
| 15 |  |  |  | 20 |  |  |  | 25 |  |  |  | 30 |  |  |  | |

```
ATT ATG GAC AAT GGA AAC ATC GAT ACA GAA TTA CTT GTT GGT ACG CTT            145
Ile Met Asp Asn Gly Asn Ile Asp Thr Glu Leu Leu Val Gly Thr Leu
             35                  40                  45

ACT CTT GGC GGC TAT AAA ACA GGA ACC ACT AGC ACA TCT GTT AAC TTT            193
Thr Leu Gly Gly Tyr Lys Thr Gly Thr Thr Ser Thr Ser Val Asn Phe
             50                  55                  60

ACA GAT GCC GCG GGT GAT CCC ATG TAC TTA ACA TTT ACT TCT CAG GAT            241
Thr Asp Ala Ala Gly Asp Pro Met Tyr Leu Thr Phe Thr Ser Gln Asp
         65                  70                  75

GGA AAT AAC CAC CAA TTC ACT ACA AAA GTG AAT GGC AAG GAT TCT AGA            289
Gly Asn Asn His Gln Phe Thr Thr Lys Val Asn Gly Lys Asp Ser Arg
         80                  85                  90

GAT TTT GAT ATC TCT CCT AAG GTA AAC GGT GAG AAC CTT GTG GGG GAT            337
Asp Phe Asp Ile Ser Pro Lys Val Asn Gly Glu Asn Leu Val Gly Asp
 95                 100                 105                 110

GAC GTC GTC TTG GCT ACG GGC AGC CAG GAT TTC TTT GTT CGC TCA ATT            385
Asp Val Val Leu Ala Thr Gly Ser Gln Asp Phe Phe Val Arg Ser Ile
                115                 120                 125

GGT TCC AAA GGC GGT AAA CTT GCA GCA GGT AAA TAC ACT GAT GCT GTA            433
Gly Ser Lys Gly Gly Lys Leu Ala Ala Gly Lys Tyr Thr Asp Ala Val
                130                 135                 140

ACC GTA ACC GTA TCT AAC CAA GGA TCC ATC GAA GGT CGT ATT AGA GCC            481
Thr Val Thr Val Ser Asn Gln Gly Ser Ile Glu Gly Arg Ile Arg Ala
                145                 150                 155

TAC GAA CAA AAC CCA CAA CAT TTT ATT GAG GAT CTA GAA AAA GTT AGG            529
Tyr Glu Gln Asn Pro Gln His Phe Ile Glu Asp Leu Glu Lys Val Arg
            160                 165                 170

GTG GAA CAA CTT ACT GGT CAT GGT TCT TCA GTT TTA GAA GAA TTG GTT            577
Val Glu Gln Leu Thr Gly His Gly Ser Ser Val Leu Glu Glu Leu Val
175                 180                 185                 190

CAG TTA GTC AAA GAT AAA AAT ATA GAT ATT TCC ATT AAA TAT GAT CCC            625
Gln Leu Val Lys Asp Lys Asn Ile Asp Ile Ser Ile Lys Tyr Asp Pro
                195                 200                 205

AGA AAA GAT TCG GAG GTT TTT GCC AAT AGA GTA ATT ACT GAT GAT ATC            673
Arg Lys Asp Ser Glu Val Phe Ala Asn Arg Val Ile Thr Asp Asp Ile
            210                 215                 220

GAA TTG CTC AAG AAA ATC CTA GCT TAT TTT CTA CCC GAG GAT GCC ATT            721
Glu Leu Leu Lys Lys Ile Leu Ala Tyr Phe Leu Pro Glu Asp Ala Ile
            225                 230                 235

CTT AAA GGC GGT CAT TAT GAC AAC CAA CTG CAA AAT GGC ATC AAG CGA            769
Leu Lys Gly Gly His Tyr Asp Asn Gln Leu Gln Asn Gly Ile Lys Arg
        240                 245                 250

GTA AAA GAG TTC CTT GAA TCA TCG CCG AAT ACA CAA TGG GAA TTG CGG            817
Val Lys Glu Phe Leu Glu Ser Ser Pro Asn Thr Gln Trp Glu Leu Arg
255                 260                 265                 270

GCG TTC ATG GCA GTA ATG CAT TTC TCT TTA ACC GCC GAT CGT ATC GAT            865
Ala Phe Met Ala Val Met His Phe Ser Leu Thr Ala Asp Arg Ile Asp
                275                 280                 285

GAT GAT ATT TTG AAA GTG ATT GTT GAT TCA ATG AAT CAT CAT GGT GAT            913
Asp Asp Ile Leu Lys Val Ile Val Asp Ser Met Asn His His Gly Asp
            290                 295                 300

GCC CGT AGC AAG TTG CGT GAA GAA TTA GCT GAG CTT ACC GCC GAA TTA            961
Ala Arg Ser Lys Leu Arg Glu Glu Leu Ala Glu Leu Thr Ala Glu Leu
        305                 310                 315

AAG ATT TAT TCA GTT ATT CAA GCC GAA ATT AAT AAG CAT CTG TCT AGT           1009
Lys Ile Tyr Ser Val Ile Gln Ala Glu Ile Asn Lys His Leu Ser Ser
320                 325                 330

AGT GGC ACC ATA AAT ATC CAT GAT AAA TCC ATT AAT CTC ATG GAT AAA           1057
```

```
Ser Gly Thr Ile Asn Ile His Asp Lys Ser Ile Asn Leu Met Asp Lys
335                 340                 345                 350

AAT TTA TAT GGT TAT ACA GAT GAA GAG ATT TTT AAA GCC AGC GCA GAG    1105
Asn Leu Tyr Gly Tyr Thr Asp Glu Glu Ile Phe Lys Ala Ser Ala Glu
                355                 360                 365

TAC AAA ATT CTC GAG AAA ATG CCT CAA ACC ACC ATT CAG GTG GAT GGG    1153
Tyr Lys Ile Leu Glu Lys Met Pro Gln Thr Thr Ile Gln Val Asp Gly
            370                 375                 380

AGC GAG AAA AAA ATA GTC TCG ATA AAG GAC TTT CTT GGA AGT GAG AAT    1201
Ser Glu Lys Lys Ile Val Ser Ile Lys Asp Phe Leu Gly Ser Glu Asn
        385                 390                 395

AAA AGA ACC GGG GCG TTG GGT AAT CTG AAA AAC TCA TAC TCT TAT AAT    1249
Lys Arg Thr Gly Ala Leu Gly Asn Leu Lys Asn Ser Tyr Ser Tyr Asn
    400                 405                 410

AAA GAT AAT AAT GAA TTA TCT CAC TTT GCC ACC ACC TGC TCG GAT AAG    1297
Lys Asp Asn Asn Glu Leu Ser His Phe Ala Thr Thr Cys Ser Asp Lys
415                 420                 425                 430

TCC AGG CCG CTC AAC GAC TTG GTT AGC CAA AAA ACA ACT CAG CTG TCT    1345
Ser Arg Pro Leu Asn Asp Leu Val Ser Gln Lys Thr Thr Gln Leu Ser
                435                 440                 445

GAT ATT ACA TCA CGT TTT AAT TCA GCT ATT GAA GCA CTG AAC CGT TTC    1393
Asp Ile Thr Ser Arg Phe Asn Ser Ala Ile Glu Ala Leu Asn Arg Phe
            450                 455                 460

ATT CAG AAA TAT GAT TCA GTG ATG CAA CGT CTG CTA GAT GAC ACG TCT    1441
Ile Gln Lys Tyr Asp Ser Val Met Gln Arg Leu Leu Asp Asp Thr Ser
        465                 470                 475

GGT AAA TGACACTAGA AGCTT                                           1462
Gly Lys
    480

(2) INFORMATION FOR SEQ ID NO:17:

(i) SEQUENCE CHARACTERISTICS:
        (A) LENGTH: 480 amino acids
        (B) TYPE: amino acid
        (D) TOPOLOGY: linear (ii) MOLECULE TYPE: protein (xi) SEQUENCE DESCRIPTION: SEQ ID NO:17:

Ala Asp Leu Thr Ala Ser Thr Thr Ala Thr Ala Thr Leu Val Glu Pro
1               5                   10                  15

Ala Arg Ile Thr Leu Thr Tyr Lys Glu Gly Ala Pro Ile Thr Ile Met
                20                  25                  30

Asp Asn Gly Asn Ile Asp Thr Glu Leu Leu Val Gly Thr Leu Thr Leu
            35                  40                  45

Gly Gly Tyr Lys Thr Gly Thr Ser Thr Ser Val Asn Phe Thr Asp
    50                  55                  60

Ala Ala Gly Asp Pro Met Tyr Leu Thr Phe Thr Ser Gln Asp Gly Asn
65                  70                  75                  80

Asn His Gln Phe Thr Thr Lys Val Asn Gly Lys Asp Ser Arg Asp Phe
                85                  90                  95

Asp Ile Ser Pro Lys Val Asn Gly Glu Asn Leu Val Gly Asp Asp Val
            100                 105                 110

Val Leu Ala Thr Gly Ser Gln Asp Phe Phe Val Arg Ser Ile Gly Ser
        115                 120                 125

Lys Gly Gly Lys Leu Ala Ala Gly Lys Tyr Thr Asp Ala Val Thr Val
    130                 135                 140

Thr Val Ser Asn Gln Gly Ser Ile Glu Gly Arg Ile Arg Ala Tyr Glu
145                 150                 155                 160
```

```
Gln Asn Pro Gln His Phe Ile Glu Asp Leu Glu Lys Val Arg Val Glu
                165                 170                 175

Gln Leu Thr Gly His Gly Ser Ser Val Leu Glu Glu Leu Val Gln Leu
            180                 185                 190

Val Lys Asp Lys Asn Ile Asp Ile Ser Ile Lys Tyr Asp Pro Arg Lys
        195                 200                 205

Asp Ser Glu Val Phe Ala Asn Arg Val Ile Thr Asp Asp Ile Glu Leu
    210                 215                 220

Leu Lys Lys Ile Leu Ala Tyr Phe Leu Pro Glu Asp Ala Ile Leu Lys
225                 230                 235                 240

Gly Gly His Tyr Asp Asn Gln Leu Gln Asn Gly Ile Lys Arg Val Lys
                245                 250                 255

Glu Phe Leu Glu Ser Ser Pro Asn Thr Gln Trp Glu Leu Arg Ala Phe
            260                 265                 270

Met Ala Val Met His Phe Ser Leu Thr Ala Asp Arg Ile Asp Asp Asp
        275                 280                 285

Ile Leu Lys Val Ile Val Asp Ser Met Asn His His Gly Asp Ala Arg
    290                 295                 300

Ser Lys Leu Arg Glu Glu Leu Ala Glu Leu Thr Ala Glu Leu Lys Ile
305                 310                 315                 320

Tyr Ser Val Ile Gln Ala Glu Ile Asn Lys His Leu Ser Ser Ser Gly
                325                 330                 335

Thr Ile Asn Ile His Asp Lys Ser Ile Asn Leu Met Asp Lys Asn Leu
            340                 345                 350

Tyr Gly Tyr Thr Asp Glu Glu Ile Phe Lys Ala Ser Ala Glu Tyr Lys
        355                 360                 365

Ile Leu Glu Lys Met Pro Gln Thr Thr Ile Gln Val Asp Gly Ser Glu
    370                 375                 380

Lys Lys Ile Val Ser Ile Lys Asp Phe Leu Gly Ser Glu Asn Lys Arg
385                 390                 395                 400

Thr Gly Ala Leu Gly Asn Leu Lys Asn Ser Tyr Ser Tyr Asn Lys Asp
                405                 410                 415

Asn Asn Glu Leu Ser His Phe Ala Thr Thr Cys Ser Asp Lys Ser Arg
            420                 425                 430

Pro Leu Asn Asp Leu Val Ser Gln Lys Thr Thr Gln Leu Ser Asp Ile
        435                 440                 445

Thr Ser Arg Phe Asn Ser Ala Ile Glu Ala Leu Asn Arg Phe Ile Gln
    450                 455                 460

Lys Tyr Asp Ser Val Met Gln Arg Leu Leu Asp Asp Thr Ser Gly Lys
465                 470                 475                 480
```

(2) INFORMATION FOR SEQ ID NO:18:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Yersinia pestis (xi) SEQUENCE DESCRIPTION: SEQ ID NO:18:

ATAAGACTGT GCTAGCTAGA GGTAATATAT G        31

(2) INFORMATION FOR SEQ ID NO:19:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Yersinia pestis (xi) SEQUENCE DESCRIPTION: SEQ ID NO:19:

GATGGATCCT TGGTTAGATA CGGTTACG        28

(2) INFORMATION FOR SEQ ID NO:20:

(i) SEQUENCE CHARACTERISTICS:
        (A) LENGTH: 547 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Yersinia pestis (ix) FEATURE:
        (A) NAME/KEY: CDS
        (B) LOCATION: 29..538

(xi) SEQUENCE DESCRIPTION: SEQ ID NO:20:

```
ATAAGACTGT GCTAGCTAGA GGTAATATAT ATG AAA AAA ATC AGT TCC GTT ATC        52
                                Met Lys Lys Ile Ser Ser Val Ile
                                 1               5

GCC ATT GCA TTA TTT GGA ACT ATT GCA ACT GCT AAT GCG GCA GAT TTA        100
Ala Ile Ala Leu Phe Gly Thr Ile Ala Thr Ala Asn Ala Ala Asp Leu
        10                  15                  20

ACT GCA AGC ACC ACT GCA ACG GCA ACT CTT GTT GAA CCA GCC CGC ATC        148
Thr Ala Ser Thr Thr Ala Thr Ala Thr Leu Val Glu Pro Ala Arg Ile
 25                  30                  35                  40

ACT CTT ACA TAT AAG GAA GGC GCT CCA ATT ACA ATT ATG GAC AAT GGA        196
Thr Leu Thr Tyr Lys Glu Gly Ala Pro Ile Thr Ile Met Asp Asn Gly
                 45                  50                  55

AAC ATC GAT ACA GAA TTA CTT GTT GGT ACG CTT ACT CTT GGC GGC TAT        244
Asn Ile Asp Thr Glu Leu Leu Val Gly Thr Leu Thr Leu Gly Gly Tyr
             60                  65                  70

AAA ACA GGA ACC ACT AGC ACA TCT GTT AAC TTT ACA GAT GCC GCG GGT        292
Lys Thr Gly Thr Thr Ser Thr Ser Val Asn Phe Thr Asp Ala Ala Gly
     75                  80                  85

GAT CCC ATG TAC TTA ACA TTT ACT TCT CAG GAT GGA AAT AAC CAC CAA        340
Asp Pro Met Tyr Leu Thr Phe Thr Ser Gln Asp Gly Asn Asn His Gln
 90                  95                 100

TTC ACT ACA AAA GTG ATT GGC AAG GAT TCT AGA GAT TTT GAT ATC TCT        388
Phe Thr Thr Lys Val Ile Gly Lys Asp Ser Arg Asp Phe Asp Ile Ser
105                 110                 115                 120
```

```
CCT AAG GTA AAC GGT GAG AAC CTT GTG GGG GAT CAG GTC GTC TTG GCT       436
Pro Lys Val Asn Gly Glu Asn Leu Val Gly Asp Gln Val Val Leu Ala
            125                 130                 135

ACG GGC AGC CAG GAT TTC TTT GTT CGC TCA ATT GGT TCC AAA GGC GGT       484
Thr Gly Ser Gln Asp Phe Phe Val Arg Ser Ile Gly Ser Lys Gly Gly
            140                 145                 150

AAA CTT GCA GCA GGT AAA TAC ACT GAT GCT GTA ACC GTA ACC GTA TCT       532
Lys Leu Ala Ala Gly Lys Tyr Thr Asp Ala Val Thr Val Thr Val Ser
            155                 160                 165

AAC CAA GGATCCATC                                                     547
Asn Gln
    170

(2) INFORMATION FOR SEQ ID NO:21:

(i) SEQUENCE CHARACTERISTICS:
        (A) LENGTH: 170 amino acids
        (B) TYPE: amino acid
        (D) TOPOLOGY: linear (ii) MOLECULE TYPE: protein (xi) SEQUENCE DESCRIPTION: SEQ ID NO:21:

Met Lys Lys Ile Ser Ser Val Ile Ala Ile Ala Leu Phe Gly Thr Ile
 1               5                  10                  15

Ala Thr Ala Asn Ala Ala Asp Leu Thr Ala Ser Thr Ala Thr Ala
            20                  25                  30

Thr Leu Val Glu Pro Ala Arg Ile Thr Leu Thr Tyr Lys Glu Gly Ala
            35                  40                  45

Pro Ile Thr Ile Met Asp Asn Gly Asn Ile Asp Thr Glu Leu Leu Val
    50                  55                  60

Gly Thr Leu Thr Leu Gly Gly Tyr Lys Thr Gly Thr Thr Ser Thr Ser
 65                  70                  75                  80

Val Asn Phe Thr Asp Ala Ala Gly Asp Pro Met Tyr Leu Thr Phe Thr
            85                  90                  95

Ser Gln Asp Gly Asn Asn His Gln Phe Thr Thr Lys Val Ile Gly Lys
            100                 105                 110

Asp Ser Arg Asp Phe Asp Ile Ser Pro Lys Val Asn Gly Glu Asn Leu
            115                 120                 125

Val Gly Asp Gln Val Val Leu Ala Thr Gly Ser Gln Asp Phe Phe Val
            130                 135                 140

Arg Ser Ile Gly Ser Lys Gly Gly Lys Leu Ala Ala Gly Lys Tyr Thr
145                 150                 155                 160

Asp Ala Val Thr Val Thr Val Ser Asn Gln
            165                 170

(2) INFORMATION FOR SEQ ID NO:22:

(i) SEQUENCE CHARACTERISTICS:
        (A) LENGTH: 1530 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Yersinia pestis
```

(ix) FEATURE:
    (A) NAME/KEY: CDS
    (B) LOCATION: 13..1515

(xi) SEQUENCE DESCRIPTION: SEQ ID NO:22:

```
TAGAGGTAAT AT ATG AAA AAA ATC AGT TCC GTT ATC GCC ATT GCA TTA            48
              Met Lys Lys Ile Ser Ser Val Ile Ala Ile Ala Leu
                1               5                  10

TTT GGA ACT ATT GCA ACT GCT AAT GCG GCA GAT TTA ACT GCA AGC ACC         96
Phe Gly Thr Ile Ala Thr Ala Asn Ala Ala Asp Leu Thr Ala Ser Thr
                15                  20                  25

ACT GCA ACG GCA ACT CTT GTT GAA CCA GCC CGC ATC ACT CTT ACA TAT        144
Thr Ala Thr Ala Thr Leu Val Glu Pro Ala Arg Ile Thr Leu Thr Tyr
        30                  35                  40

AAG GAA GGC GCT CCA ATT ACA ATT ATG GAC AAT GGA AAC ATC GAT ACA        192
Lys Glu Gly Ala Pro Ile Thr Ile Met Asp Asn Gly Asn Ile Asp Thr
 45                  50                  55                  60

GAA TTA CTT GTT GGT ACG CTT ACT CTT GGC GGC TAT AAA ACA GGA ACC        240
Glu Leu Leu Val Gly Thr Leu Thr Leu Gly Gly Tyr Lys Thr Gly Thr
                    65                  70                  75

ACT AGC ACA TCT GTT AAC TTT ACA GAT GCC GCG GGT GAT CCC ATG TAC        288
Thr Ser Thr Ser Val Asn Phe Thr Asp Ala Ala Gly Asp Pro Met Tyr
             80                  85                  90

TTA ACA TTT ACT TCT CAG GAT GGA AAT AAC CAC CAA TTC ACT ACA AAA        336
Leu Thr Phe Thr Ser Gln Asp Gly Asn Asn His Gln Phe Thr Thr Lys
         95                 100                 105

GTG ATT GGC AAG GAT TCT AGA GAT TTT GAT ATC TCT CCT AAG GTA AAC        384
Val Ile Gly Lys Asp Ser Arg Asp Phe Asp Ile Ser Pro Lys Val Asn
    110                 115                 120

GGT GAG AAC CTT GTG GGG GAT GAC GTC GTC TTG GCT ACG GGC AGC CAG        432
Gly Glu Asn Leu Val Gly Asp Asp Val Val Leu Ala Thr Gly Ser Gln
125                 130                 135                 140

GAT TTC TTT GTT CGC TCA ATT GGT TCC AAA GGC GGT AAA CTT GCA GCA        480
Asp Phe Phe Val Arg Ser Ile Gly Ser Lys Gly Gly Lys Leu Ala Ala
                145                 150                 155

GGT AAA TAC ACT GAT GCT GTA ACC GTA ACC GTA TCT AAC CAA GGA TCC        528
Gly Lys Tyr Thr Asp Ala Val Thr Val Thr Val Ser Asn Gln Gly Ser
            160                 165                 170

ATC GAA GGT CGT ATT AGA GCC TAC GAA CAA AAC CCA CAA CAT TTT ATT        576
Ile Glu Gly Arg Ile Arg Ala Tyr Glu Gln Asn Pro Gln His Phe Ile
        175                 180                 185

GAG GAT CTA GAA AAA GTT AGG GTG GAA CAA CTT ACT GGT CAT GGT TCT        624
Glu Asp Leu Glu Lys Val Arg Val Glu Gln Leu Thr Gly His Gly Ser
    190                 195                 200

TCA GTT TTA GAA GAA TTG GTT CAG TTA GTC AAA GAT AAA AAT ATA GAT        672
Ser Val Leu Glu Glu Leu Val Gln Leu Val Lys Asp Lys Asn Ile Asp
205                 210                 215                 220

ATT TCC ATT AAA TAT GAT CCC AGA AAA GAT TCG GAG GTT TTT GCC AAT        720
Ile Ser Ile Lys Tyr Asp Pro Arg Lys Asp Ser Glu Val Phe Ala Asn
                225                 230                 235

AGA GTA ATT ACT GAT GAT ATC GAA TTG CTC AAG AAA ATC CTA GCT TAT        768
Arg Val Ile Thr Asp Asp Ile Glu Leu Leu Lys Lys Ile Leu Ala Tyr
            240                 245                 250

TTT CTA CCC GAG GAT GCC ATT CTT AAA GGC GGT CAT TAT GAC AAC CAA        816
Phe Leu Pro Glu Asp Ala Ile Leu Lys Gly Gly His Tyr Asp Asn Gln
        255                 260                 265

CTG CAA AAT GGC ATC AAG CGA GTA AAA GAG TTC CTT GAA TCA TCG CCG        864
Leu Gln Asn Gly Ile Lys Arg Val Lys Glu Phe Leu Glu Ser Ser Pro
    270                 275                 280

AAT ACA CAA TGG GAA TTG CGG GCG TTC ATG GCA GTA ATG CAT TTC TCT        912
Asn Thr Gln Trp Glu Leu Arg Ala Phe Met Ala Val Met His Phe Ser
```

```
                285                 290                 295                 300

TTA ACC GCC GAT CGT ATC GAT GAT GAT ATT TTG AAA GTG ATT GTT GAT    960
Leu Thr Ala Asp Arg Ile Asp Asp Asp Ile Leu Lys Val Ile Val Asp
                305                 310                 315

TCA ATG AAT CAT CAT GGT GAT GCC CGT AGC AAG TTG CGT GAA GAA TTA    1008
Ser Met Asn His His Gly Asp Ala Arg Ser Lys Leu Arg Glu Glu Leu
                320                 325                 330

GCT GAG CTT ACC GCC GAA TTA AAG ATT TAT TCA GTT ATT CAA GCC GAA    1056
Ala Glu Leu Thr Ala Glu Leu Lys Ile Tyr Ser Val Ile Gln Ala Glu
                335                 340                 345

ATT AAT AAG CAT CTG TCT AGT AGT GGC ACC ATA AAT ATC CAT GAT AAA    1104
Ile Asn Lys His Leu Ser Ser Ser Gly Thr Ile Asn Ile His Asp Lys
            350                 355                 360

TCC ATT AAT CTC ATG GAT AAA AAT TTA TAT GGT TAT ACA GAT GAA GAG    1152
Ser Ile Asn Leu Met Asp Lys Asn Leu Tyr Gly Tyr Thr Asp Glu Glu
365                 370                 375                 380

ATT TTT AAA GCC AGC GCA GAG TAC AAA ATT CTC GAG AAA ATG CCT CAA    1200
Ile Phe Lys Ala Ser Ala Glu Tyr Lys Ile Leu Glu Lys Met Pro Gln
                385                 390                 395

ACC ACC ATT CAG GTG GAT GGG AGC GAG AAA AAA ATA GTC TCG ATA AAG    1248
Thr Thr Ile Gln Val Asp Gly Ser Glu Lys Lys Ile Val Ser Ile Lys
                400                 405                 410

GAC TTT CTT GGA AGT GAG AAT AAA AGA ACC GGG GCG TTG GGT AAT CTG    1296
Asp Phe Leu Gly Ser Glu Asn Lys Arg Thr Gly Ala Leu Gly Asn Leu
            415                 420                 425

AAA AAC TCA TAC TCT TAT AAT AAA GAT AAT AAT GAA TTA TCT CAC TTT    1344
Lys Asn Ser Tyr Ser Tyr Asn Lys Asp Asn Asn Glu Leu Ser His Phe
        430                 435                 440

GCC ACC ACC TGC TCG GAT AAG TCC AGG CCG CTC AAC GAC TTG GTT AGC    1392
Ala Thr Thr Cys Ser Asp Lys Ser Arg Pro Leu Asn Asp Leu Val Ser
445                 450                 455                 460

CAA AAA ACA ACT CAG CTG TCT GAT ATT ACA TCA CGT TTT AAT TCA GCT    1440
Gln Lys Thr Thr Gln Leu Ser Asp Ile Thr Ser Arg Phe Asn Ser Ala
                465                 470                 475

ATT GAA GCA CTG AAC CGT TTC ATT CAG AAA TAT GAT TCA GTG ATG CAA    1488
Ile Glu Ala Leu Asn Arg Phe Ile Gln Lys Tyr Asp Ser Val Met Gln
                480                 485                 490

CGT CTG CTA GAT GAC ACG TCT GGT AAA TGACACTAGA AGCTT              1530
Arg Leu Leu Asp Asp Thr Ser Gly Lys
                495                 500

(2) INFORMATION FOR SEQ ID NO:23:

(i) SEQUENCE CHARACTERISTICS:
        (A) LENGTH: 501 amino acids
        (B) TYPE: amino acid
        (D) TOPOLOGY: linear (ii) MOLECULE TYPE: protein (xi) SEQUENCE DESCRIPTION: SEQ ID NO:23:

Met Lys Lys Ile Ser Ser Val Ile Ala Ile Ala Leu Phe Gly Thr Ile
 1               5                  10                  15

Ala Thr Ala Asn Ala Ala Asp Leu Thr Ala Ser Thr Thr Ala Thr Ala
                20                  25                  30

Thr Leu Val Glu Pro Ala Arg Ile Thr Leu Thr Tyr Lys Glu Gly Ala
            35                  40                  45

Pro Ile Thr Ile Met Asp Asn Gly Asn Ile Asp Thr Glu Leu Leu Val
        50                  55                  60

Gly Thr Leu Thr Leu Gly Gly Tyr Lys Thr Gly Thr Thr Ser Thr Ser
65                  70                  75                  80
```

-continued

Val Asn Phe Thr Asp Ala Ala Gly Asp Pro Met Tyr Leu Thr Phe Thr
            85                  90                  95

Ser Gln Asp Gly Asn Asn His Gln Phe Thr Thr Lys Val Ile Gly Lys
            100                 105                 110

Asp Ser Arg Asp Phe Asp Ile Ser Pro Lys Val Asn Gly Glu Asn Leu
            115                 120                 125

Val Gly Asp Asp Val Val Leu Ala Thr Gly Ser Gln Asp Phe Phe Val
            130                 135                 140

Arg Ser Ile Gly Ser Lys Gly Lys Leu Ala Ala Gly Lys Tyr Thr
145                 150                 155                 160

Asp Ala Val Thr Val Thr Val Ser Asn Gln Gly Ser Ile Glu Gly Arg
            165                 170                 175

Ile Arg Ala Tyr Glu Gln Asn Pro Gln His Phe Ile Glu Asp Leu Glu
            180                 185                 190

Lys Val Arg Val Glu Gln Leu Thr Gly His Gly Ser Ser Val Leu Glu
            195                 200                 205

Glu Leu Val Gln Leu Val Lys Asp Lys Asn Ile Asp Ile Ser Ile Lys
            210                 215                 220

Tyr Asp Pro Arg Lys Asp Ser Glu Val Phe Ala Asn Arg Val Ile Thr
225                 230                 235                 240

Asp Asp Ile Glu Leu Lys Lys Ile Leu Ala Tyr Phe Leu Pro Glu
            245                 250                 255

Asp Ala Ile Leu Lys Gly Gly His Tyr Asp Asn Gln Leu Gln Asn Gly
            260                 265                 270

Ile Lys Arg Val Lys Glu Phe Leu Glu Ser Ser Pro Asn Thr Gln Trp
            275                 280                 285

Glu Leu Arg Ala Phe Met Ala Val Met His Phe Ser Leu Thr Ala Asp
            290                 295                 300

Arg Ile Asp Asp Ile Leu Lys Val Ile Val Asp Ser Met Asn His
305                 310                 315                 320

His Gly Asp Ala Arg Ser Lys Leu Arg Glu Glu Leu Ala Glu Leu Thr
            325                 330                 335

Ala Glu Leu Lys Ile Tyr Ser Val Ile Gln Ala Glu Ile Asn Lys His
            340                 345                 350

Leu Ser Ser Ser Gly Thr Ile Asn Ile His Asp Lys Ser Ile Asn Leu
            355                 360                 365

Met Asp Lys Asn Leu Tyr Gly Tyr Thr Asp Glu Glu Ile Phe Lys Ala
            370                 375                 380

Ser Ala Glu Tyr Lys Ile Leu Glu Lys Met Pro Gln Thr Thr Ile Gln
385                 390                 395                 400

Val Asp Gly Ser Glu Lys Lys Ile Val Ser Ile Lys Asp Phe Leu Gly
            405                 410                 415

Ser Glu Asn Lys Arg Thr Gly Ala Leu Gly Asn Leu Lys Asn Ser Tyr
            420                 425                 430

Ser Tyr Asn Lys Asp Asn Asn Glu Leu Ser His Phe Ala Thr Thr Cys
            435                 440                 445

Ser Asp Lys Ser Arg Pro Leu Asn Asp Leu Val Ser Gln Lys Thr Thr
            450                 455                 460

Gln Leu Ser Asp Ile Thr Ser Arg Phe Asn Ser Ala Ile Glu Ala Leu
465                 470                 475                 480

Asn Arg Phe Ile Gln Lys Tyr Asp Ser Val Met Gln Arg Leu Leu Asp
            485                 490                 495

Asp Thr Ser Gly Lys

```
        500

(2) INFORMATION FOR SEQ ID NO:24:

(i) SEQUENCE CHARACTERISTICS:
          (A) LENGTH: 24 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: NO (iv) ANTI-SENSE: NO (vi) ORIGINAL SOURCE:
          (A) ORGANISM: Yersinia pestis (xi) SEQUENCE DESCRIPTION: SEQ ID NO:24:

GATCGAATTC GAGCCTACGA ACAA                                              24
```